(12) United States Patent
Mercanzini et al.

(10) Patent No.: US 11,344,728 B2
(45) Date of Patent: May 31, 2022

(54) NEUROSTIMULATION DEVICE WITH RECORDING PATCH

(71) Applicant: ALEVA NEUROTHERAPEUTICS, Lausanne (CH)

(72) Inventors: Andre Mercanzini, Saint Sulpice (CH); Alain Dransart, Lausanne (CH); Khoa Nguyen, Lausanne (CH)

(73) Assignee: ALEVA NEUROTHERAPEUTICS, Lausanne (CH)

( * ) Notice: Subject to any disclaimer, the term of this patent is extended or adjusted under 35 U.S.C. 154(b) by 375 days.

(21) Appl. No.: 16/424,044

(22) Filed: May 28, 2019

(65) Prior Publication Data

US 2020/0376276 A1    Dec. 3, 2020

(51) Int. Cl.
| | | |
|---|---|---|
| *A61N 1/36* | (2006.01) | |
| *A61N 1/05* | (2006.01) | |
| *A61N 1/08* | (2006.01) | |
| *A61N 1/372* | (2006.01) | |
| *G16H 20/30* | (2018.01) | |
| *A61B 5/00* | (2006.01) | |
| *A61B 5/24* | (2021.01) | |

(52) U.S. Cl.
CPC ....... *A61N 1/36135* (2013.01); *A61N 1/0534* (2013.01); *A61N 1/08* (2013.01); *A61N 1/3606* (2013.01); *A61N 1/37211* (2013.01); *A61B 5/24* (2021.01); *A61B 5/6868* (2013.01); *G16H 20/30* (2018.01)

(58) Field of Classification Search
None
See application file for complete search history.

(56) References Cited

U.S. PATENT DOCUMENTS

| | | | |
|---|---|---|---|
| 6,248,080 B1* | 6/2001 | Miesel | A61B 5/0215 |
| | | | 600/311 |
| 8,792,972 B2 | 7/2014 | Zaidel et al. | |
| 9,814,885 B2* | 11/2017 | Molnar | A61N 1/0529 |
| 10,166,392 B2* | 1/2019 | Mercanzini | A61N 1/36082 |
| 10,471,259 B2* | 11/2019 | Stanslaski | A61N 1/3615 |
| 10,758,174 B2* | 9/2020 | Widge | A61B 5/4064 |
| 2009/0082691 A1* | 3/2009 | Denison | A61B 5/374 |
| | | | 600/544 |
| 2011/0264165 A1 | 10/2011 | Molnar et al. | |
| 2012/0101552 A1 | 4/2012 | Lazarewicz et al. | |
| 2014/0128937 A1* | 5/2014 | Deere | A61N 1/36128 |
| | | | 607/45 |
| 2017/0042474 A1* | 2/2017 | Widge | A61N 1/36135 |
| 2018/0243564 A1 | 8/2018 | Stanslaski et al. | |

FOREIGN PATENT DOCUMENTS

WO    WO-2017/158067 A1    9/2017

OTHER PUBLICATIONS

Foreign Search Report on EP 20176903.1 dated Mar. 29, 2021.

* cited by examiner

*Primary Examiner* — Shirley X Jian
(74) *Attorney, Agent, or Firm* — Foley & Lardner LLP

(57) ABSTRACT

The present disclosure describes systems and methods for recording electrical activity, such as local field potentials. The system can include a recording patch that is placed inline between an implanted neurological lead and an implantable pulse stimulator. The recording patch can include recording and amplification circuitry that detects, records, and amplifies electrical activity (also referred to as signals) from a target site. The system can be used to select over which of the lead's electrodes therapeutic stimulations are delivered.

20 Claims, 15 Drawing Sheets

NEUROSTIMULATION DEVICE WITH RECORDING PATCH

BACKGROUND OF THE DISCLOSURE

Deep brain stimulation (DBS) is a neurostimulation therapy that can involve electrical stimulation systems that stimulate the human brain and body. DBS can be used to treat a number of neurological disorders. Typically, DBS involves electrically stimulating a target area of the brain.

SUMMARY OF THE DISCLOSURE

The present disclosure describes systems and methods for recording electrical activity, such as local field potentials. The system can include a recording patch that is placed inline between an implanted neurological lead and an implantable pulse stimulator. The recording patch can include recording and amplification circuitry that detects, records, and amplifies electrical activity (also referred to as signals) from a target site. The system can be used to select over which of the lead's electrodes to deliver therapeutic stimulations. The system can select the electrodes based on the amount of power within the beta band of the signal or other characteristics of the signal.

According to at least one aspect of the disclosure, an implantable device can include a first port. The first port can be configured to receive a connection from an implantable pulse stimulator. The first port can include a first plurality of connections. The device can include a second port. The second port can be configured to receive a connection from an implantable lead. The second port can include a second plurality of connections. The device can include a plurality of switches. The switches can be configured to selectively interconnect, at a first time point, the first plurality of connections with the second plurality of connections to pass a stimulation signal from the implantable pulse stimulator to the implantable lead. The switches can selectively interconnect, at a second time point, the second plurality of connections with a recording module. The recording module can generate an amplified biological signal based on a biological signal received from the second plurality of connections. The recording module can transmit the amplified biological signal to a receiver.

According to at least one aspect of the disclosure, a method can include implanting a recording patch into a subject. The recording patch can include a first port that can be configured to receive a connection from an implantable pulse stimulator. The first port can include a first plurality of connections. The recording patch can include a second port that can be configured to receive a connection from an implantable lead that can include a plurality of electrodes. The second port can include a second plurality of connections. The recording patch can include a plurality of switches in electrical communication with the first plurality of connections and the second plurality of connections. The recording patch can include a recording module. The method can include coupling, with the plurality of switches, the second plurality of connections with the recording module. The method can include receiving, at the second plurality of connections, biological signals from the implantable lead. The method can include generating, by the recording module, amplified biological signals based on the biological signals. The method can include determining at least one signal characteristic of the biological signals. The method can include selecting an electrode of the plurality of electrodes based on the at least one signal characteristic of the biological signal.

BRIEF DESCRIPTION OF THE DRAWINGS

The accompanying drawings are not intended to be drawn to scale. Like reference numbers and designations in the various drawings indicate like elements. For purposes of clarity, not every component may be labelled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a technical solution for performing neural recordings and stimulations. The system can include a recording patch that can be coupled inline between an implanted pulse stimulator and a lead implanted into, for example, a subject's brain. The recording patch can receive biological signals from the subject's brain and can amplify the biological signals. The biological signals can be any electrophysiological signal generated by the patient, such as local field potentials, single units, neural ensembles, or other electrical signals generated by patient's brain or body. The recording patch transmit the amplified signals to an external device. The external device can also provide wireless power to the recording patch. The signals collected by the recording patch can be used to guide the subject's therapy. For example, the recording patch or external device associated with the recording patch can select stimulation electrodes based on power distributions within specific frequency bands of the amplified signals. When not in use, the recording patch can be placed into a pass-through mode that enables the stimulation signals from the pulse stimulator to pass substantially unchanged through the recording patch to the lead.

Figure 1:
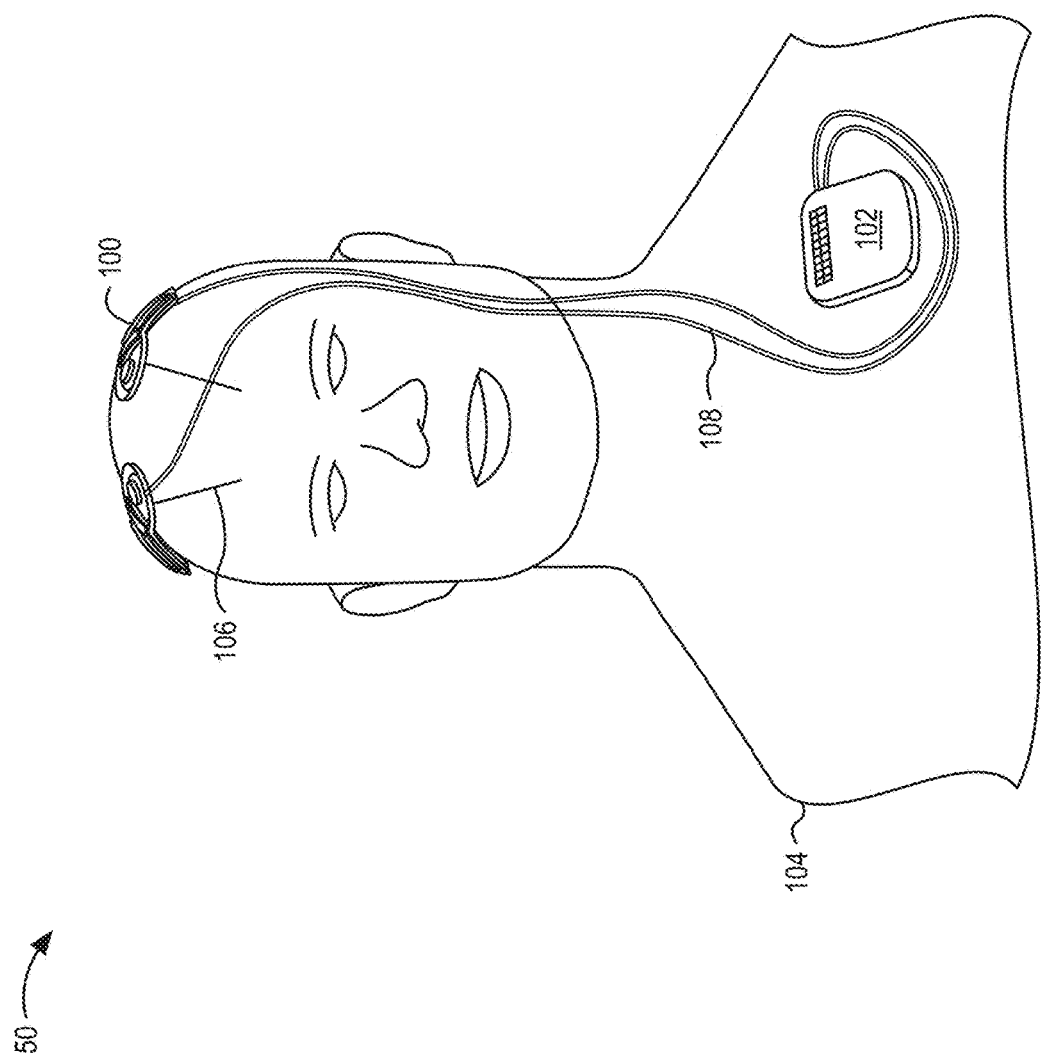
FIG. 1 illustrates a front view of a subject implanted with an example system for performing neurostimulation.
Figure 2:
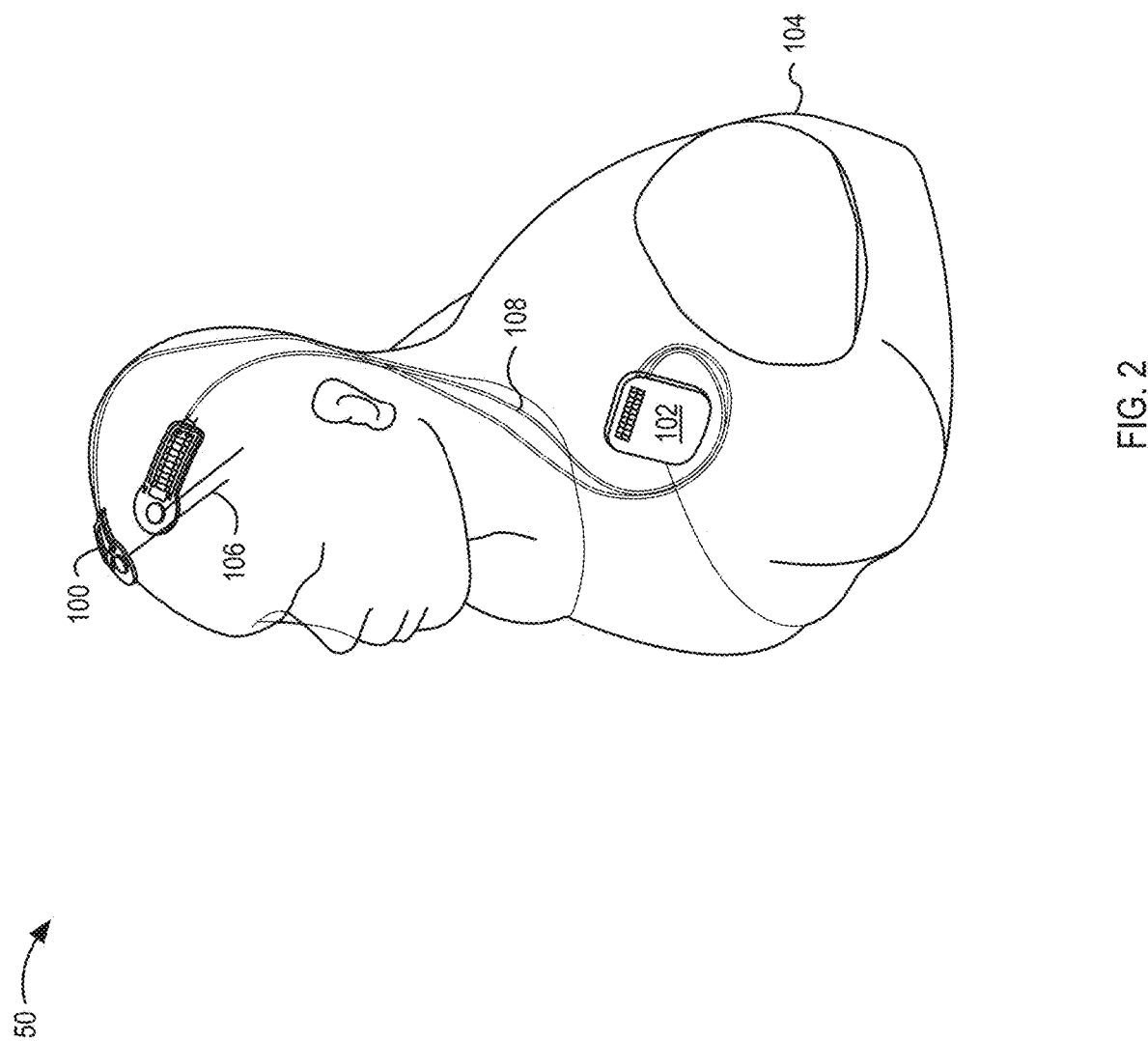
FIG. 2 illustrates a perspective view of the subject implanted with the example system for performing neurostimulation.
Figure 3:
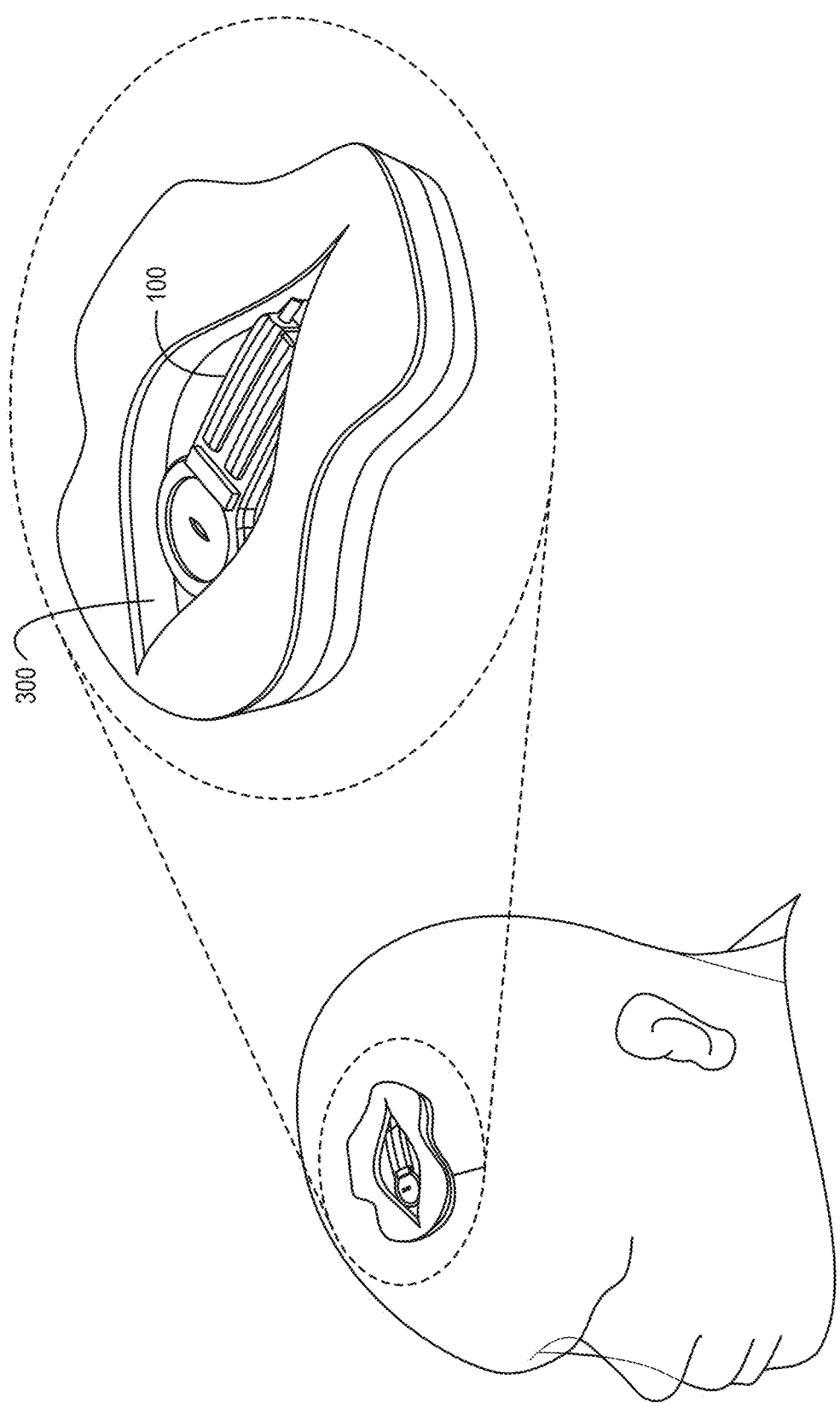
FIG. 3 illustrates an enlarged view of the recording patch implanted below the subject's scalp.

FIG. 1 illustrates a front view of a subject implanted with an example system 50 for performing neurostimulation. FIG. 2 illustrates a perspective view of the subject implanted with the example system 50 for performing neurostimulation. FIG. 3 illustrates an enlarged view of the recording patch 100 implanted below the subject's scalp 300.

The system 50 includes a recording patch 100 implanted below the subject's scalp. The recording patch 100 is coupled with an implantable pulse stimulator 102, which is implanted into the subject 104. The recording patch 100 is also coupled with an implantable lead 106. An implantable lead 106 can be implanted into each hemisphere of the subject's brain (or other location within the subject). The recording patch 100 can be coupled with the pulse generator 102 and the leads 106 via cables 108.

The system 50 can include one or more recording patches 100. The recording patches 100 are described further in relation to FIGS. 3-9, among others. The recording patch 100 can improve (or provide) the recording capabilities for the implantable pulse stimulator 102. The pulse stimulator 102 can be a stimulation only device (e.g., the pulse stimulator 102 may not include recording capabilities) and the recording patch 100 can perform electrical recordings that are used to monitor the subject's response to electrical stimulations and coordinate the subject's therapy.

The recording patch 100 can be placed inline between the implantable pulse stimulator 102 and the leads 106. The implantable pulse stimulator 102 can be configured to deliver electrical stimulation to the subject via the leads 106.

The recording patch 100 can amplify electrical signals (e.g., biological signals) detected by the electrodes of the leads 106. The recording patch 100 can amplify the signals and transmit the amplified signals externally from the subject to, for example, an external programmer, which can also be referred to as a receiver. The recording patch 100 can calculate or determine one or more characteristics of the signals and transmit the characteristics of the signal externally from the subject. In some cases, the recording patch 100 can transmit the amplified signals to an external programmer that can calculate the signal characteristics. The signal characteristics can include power distributions within specific frequency ranges of the amplified signals.

The leads 106 can record or detect local field potentials (LFPs). LFPs can be low frequency fluctuations of electrical activity below about 500 Hz. LFPs can represent the spatial-temporal summation of postsynaptic potentials from local neuronal ensembles in the vicinity of the electrode. The LFPs can be viewed as a metric of neuronal synchronization. In Parkinson's subjects, a suppression of beta activity by high-frequency stimulation of the subthalamic nucleus can lead to motor improvements.

The recording patch 100 can select one or more of the lead's electrodes as stimulating electrodes. The selection of the stimulating electrodes can be based on the signals (or the characteristics thereof) detected or recorded at the recording patch 100. For example, the recording patch 100 can select the electrodes for stimulation that include the most power within the beta band.

When the recording patch 100 is not being used to actively record signals from the subject 104, the recording patch 100 can be placed into a stimulation mode (which can also be referred to as a pass-through mode) and can transmit or forward stimulation signals from the implantable pulse stimulator 102 to the leads 106. In the pass-through mode, the recording patch 100 does not substantially affect the stimulation signal generated by the implantable pulse stimulator 102 as the stimulation signal passes through the recording patch 100. For example, the voltage and current of the stimulation signal can be substantially the same when entering and exiting the recording patch 100.

The implantable pulse stimulator 102 can generate therapeutic, electrical stimulations that can be delivered to the subject's brain or other locations by leads 106. The implantable pulse stimulator 102 can be implanted into the subject 104 at a surgical site remote to the recording patch 100 and the leads 106. For example, the implantable pulse stimulator 102 can be implanted into a surgically created pocket in the subject's chest, between the skin and muscle. The implantable pulse stimulator 102 can generate stimulation signals that pass to the subject 104 via the cables 108, recording patch 100, and lead 106. The stimulation signal can include a plurality of wave forms including, but not limited to, pulses, charged balanced pulses, sinusoidal waves, square waves, triangle waves, and combinations thereof. The electrical stimulation can provide a therapeutic benefit to the subject, such as, suppressing beta activity.

The implantable pulse stimulator 102 can be a stimulating only device. For example, the implantable pulse stimulator 102 does not receive biological signals from the subject. The implantable pulse stimulator 102 can be a stimulating and recording device. For example, the implantable pulse stimulator 102 can both generate and output stimulation signals and also receive biological signals that the implantable pulse stimulator 102 digitizes and stores.

The system 50 can include a plurality of cables 108. One or more cables 108 can interconnect the recording patch 100 and the implantable pulse stimulator 102 and the recording patch 100 and the leads 106. Each cable 108 can include a plurality of conductors to independently carry a plurality of signals between the components connected with the cable 108. For example, the lead 106 can have 12 electrodes and the cable 108 can include a dedicated conductor for each of the different electrodes. For each conductor within the cable 108, the cable 108 can include a terminal or connector at each end of the cable 108.

The system 50 can include one or more leads 106. The system 50 can include a lead 106 for each recording patch 100. The lead 106 can be a multielectrode lead. The lead 106 can include a distal end and a proximal end. The distal end can include a plurality of electrodes. The proximal end can include a plurality of terminal contacts. Each of the terminal contacts can be electrically coupled with at least one of the electrodes. For example, a wire (or other electrical trace) can run through the interior of the lead 106 from one of the terminal contacts to a contact disposed toward the distal end that is in electrical communication with the electrode. The lead 106 can be a MEMS-based lead 106. For example, the lead 106 can include a MEMS film that includes a plurality of electrodes. The MEMS film can be manufactured as a planar film. The MEMS film can be heated and molded to form a cylinder. The cylinder can be backfilled with a polymer to electrically encapsulate the connections of the lead 106 and fill the cylinder's lumen. The lead 106 can be a lead as described in U.S. Pat. No. 9,474,894, which is herein incorporated by reference in its entirety.

Figure 4:
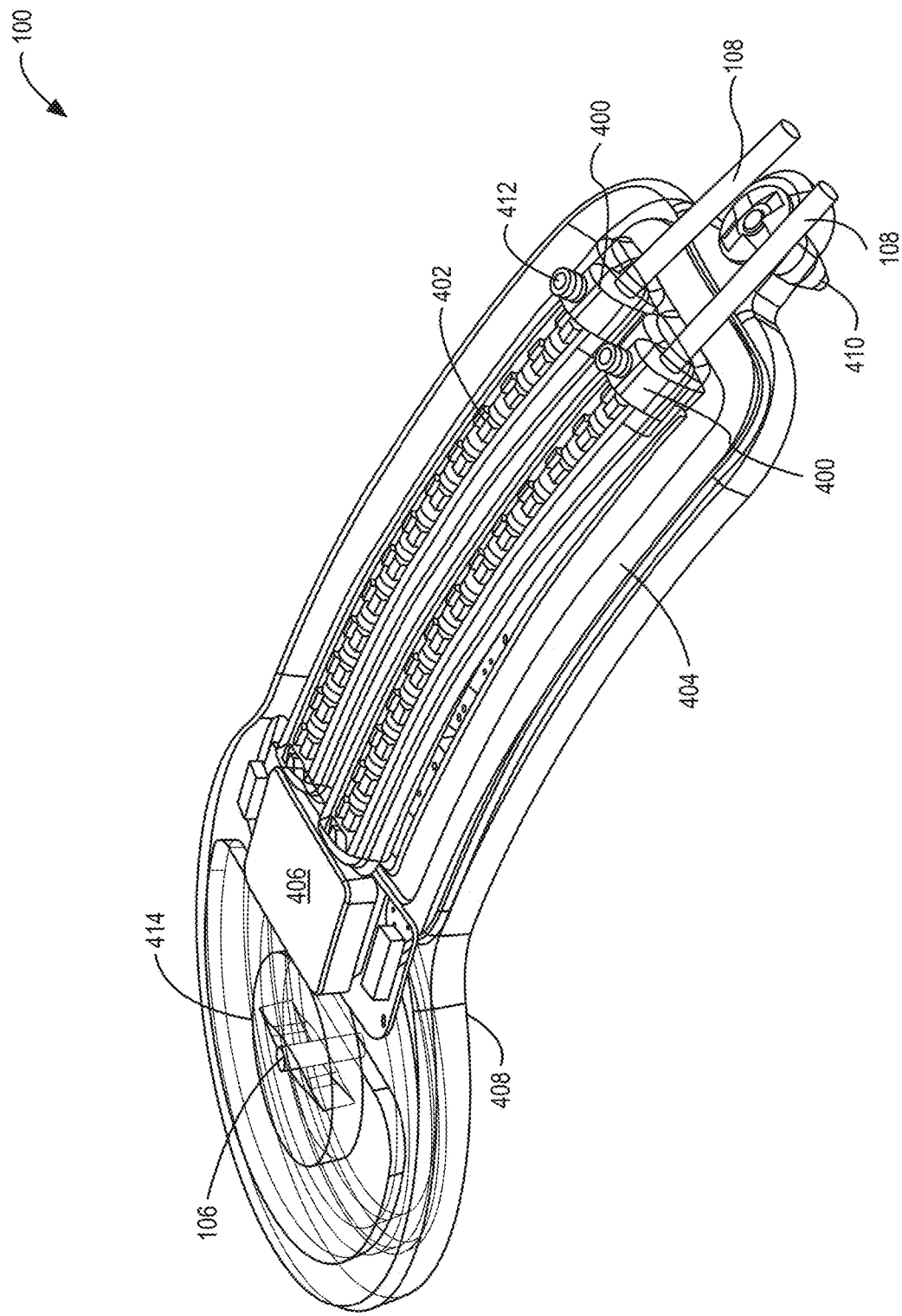
FIGS. 4-6 illustrate enlarged views of the recording patch illustrated in FIGS. 1-3.
Figure 5:
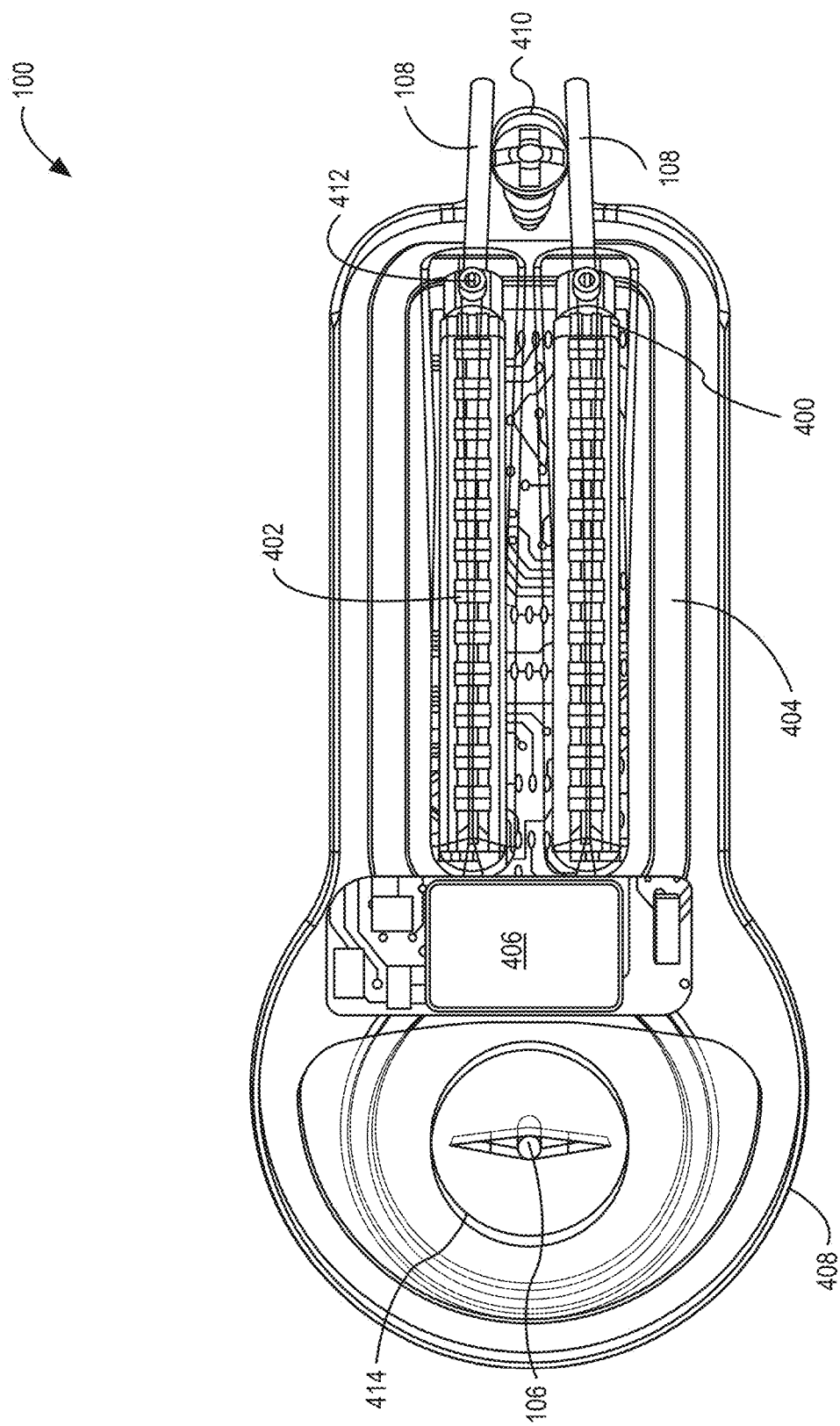
Figure 6:
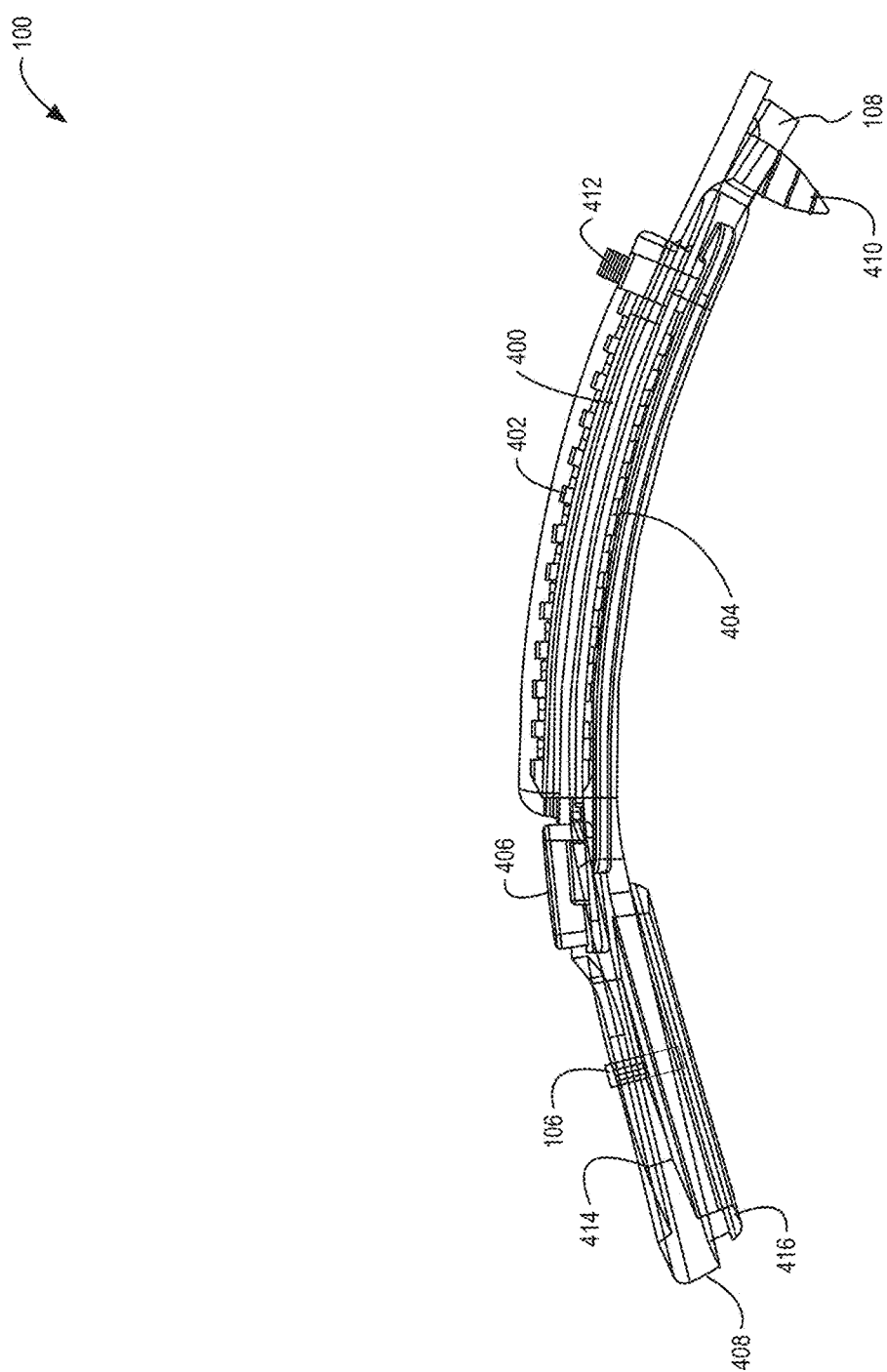

FIGS. 4-6 illustrate enlarged views of the recording patch 100. The recording patch 100 can include a plurality of ports 400. The ports 400 can include a plurality of connections 402. The ports 400 can include screws 412 to secure the cables 108 into the ports 400. The recording patch 100 can include an antenna 404 for receiving power from an external source and to transmit and receive data with an external source. The recording patch 100 can include a controller 406 to control data exchange and a plurality of switches that interconnect the ports 400 with a recording module. The housing 408 of the recording patch 100 can include a pass-through port 414 through which the lead 106 passes.

The housing 408 can include a screw 410 that can be used to secure the recording patch 100 to the subject's skull.

The recording patch 100 can include a plurality of ports 400. The recording patch 100 can include a first port 400 and a second port 400. One of the ports 400 can be configured to receive a connection from the pulse stimulator 102. One of the ports 400 can be configured to receive a connection from the lead 106.

The ports 400 can be male connections, female connections, or a combination thereof. For example, one port 400 can be a female connector and a second port 400 can be a male connector. The ports 400 can each include a plurality of connections 402. For example, for a female port 400, the plurality of connections 402 can be distributed along the axial length of the port's internal lumen. For a male port 400, the connections 402 can be distributed along the axial length of the port's barrel.

Each of the connections 402 can be ring-based electrical contacts. At each axial position of the connections 402 along the port 400, the connections 402 can include a metal layer around the circumference of the port's lumen. The connections 402 can be springed or hinged pins that can depress onto a contact of the cable 108 when the cable 108 is inserted into the port 400. The cable 108 can include a plurality of contacts along its tip. Each of the cable's contacts can align with one of the connections 402 when the cable 108 is inserted into the port 400. Each port can include between about 2 and about 64, between about 6 and about 64, between about 12 and about 64, or between about 8 and about 32 connections 402. The connections 402 can include Platinum-Iridium, MP35N, or other medical implantable conductive metal.

The port 400 can include a mechanism to secure the cable 108 to the recording patch 100. For example, each port 400 can include a screw 412. The screw 412 can be a blunt tipped screw such that the screw 412 does not puncture the cable 108. Once the cable 108 is inserted into the port 400, the screw 412 can be tightened onto the cable 108 to secure the cable 108 in place. The mechanism to secure the cable 108 into place can include a lure-lock or other type of latching system.

The recording patch 100 can include an antenna 404. The antenna 404 can be a wire coil that is embedded within the body of the housing 408. The antenna 404 can be a plurality of electrical traces etched onto a circuit board to which the other components (e.g., the controller 406 and power supply) are coupled.

The diameter of the antenna 404 can be selected to enable the antenna 404 to efficiently couple with an external source, such as an external programmer, power source, or data storage device (each of these functions can be performed by a single, external device). The antenna 404 can enable the recording patch 100 to wirelessly communicate with an external programmer over the 27 MHz frequency. Other frequencies which could be used are any of those determined by the International Telecommunication Union Radiocommunication Sector (ITU-R) in their reserved Industrial, Scientific, and Medical (ISM) Bands such as for example, but not limited to, 6.780 Mhz, 13.560 MHz, 40.680 MHz, 2.450 GHz, 5.80 GHz. The antenna diameter can be inversely proportional to the wavelength of the signal the antenna 404 transmits over. For example, with a 27 MHz frequency the loop diameter of the antenna 404 can be about 25 mm in diameter. In general, the loop diameter of the antenna is about half the wavelength of the frequency used to communicate with the antenna.

The antenna 404 can be used to inductively receive power from an external power source. The recording patch 100 can have no internal power source. In this case the inductively coupled power from the external source can be used to power the recording patch 100. The external power source can provide sufficient power to power the recording patch 100 during recording operations. For example, the recording patch 100 can inductively receive between about 5 mW and about 15 mW when in operation. The recording patch 100 can include an internal power source, such as a battery. The recording patch 100 can recharge the battery by inductively receiving power via the antenna 404, which is stored in the battery.

The antenna 404 can be used to transmit data between the recording patch 100 and an external source. For example, the recording patch 100 can receive electrical signals from the lead 106. The electrical signals can be biological signals, such as electrical signals generated by the subject's brain. The recording patch 100 can amplify the received signals. The recording patch 100 can digitize the signals. The recording patch 100 can transmit the digitized signals to the external source via the antenna 404. The antenna 404 can also receive configuration information from the external source. For example, via the antenna 404, the recording patch 100 can receive configuration information that puts the recording patch 100 into a pass-through mode or a recording mode. The configuration information can include connection information. The connection information can include instructions for the interconnection of the first port's connections 402 with the second port's connections 402.

The recording patch 100 can include a controller 406. The controller 406 is also described further in relation to FIG. 8, among others. The controller 406 can include one or more amplifies. For example, the controller 406 can include an amplifier for each of the channels coming into the recording patch 100 from the lead 106. The amplifiers can be configured to amplify the signals before the signals are transmitted to an external source.

The controller 406 can include different modules. For example, the controller 406 can include a recording module that controls the recording and digitization of the signals coming into the recording patch 100 from the lead 106. The controller 406 can include a selector module. The selector module can determine which of the lead's electrodes should be used to deliver electrical stimulation to the subject. For example, based on a power distribution within the beta band, the selector module can select and configure which of the connections in the port 400 going to the lead 106 should be coupled with connections in port 400 going to the pulse stimulator 102.

The selector module can select the electrodes to use for stimulation based on the signal characteristics of the signals received from the lead 106. The characteristics can be the amount of power in a beta band of the received signals. The beta band can be between about 10 Hz and about 30 Hz, for example. The selector module can select the electrodes that include the most power in the beta band.

The components of the recording patch 100 can be enclosed within a housing 408. For example, the controller 406 and the antenna 404 can be contained within an internal space of the housing 408. The housing 408 can be manufactured from plastic or be a hermetically sealed titanium case. The housing 408 is molded around the components of the recording patch 100. The housing 408 can include one or more electrode sites to enable the housing 408 to be used as a ground or reference for the recordings made at the lead 106. The housing 408 can be metal and the housing 408 itself can be used as a ground or reference electrode. The housing 408 can be implemented in Titanium, Titanium Dioxide, Ceramic, Polymer, or any material that conductive or capacitive, biocompatible, and maintains the inner contents sealed.

The housing 408 can include a convex shape that enables the recording patch 100 to be secure against the subject's skull. The convex shape of the recording patch 100 can substantially match the curvature of the subject's skull. The housing 408 can be flexible to conform to the curvature of the subject's skull. The housing 408 can be secured to the subject's skull with a screw 410.

The housing 408 can include a pass-through port 414. The pass-through port 414 can be configured to receive and hold the lead 106 or body thereof. The pass-through port 414 can include a lip 416 that mates with the burr hole (in the subject's skull) through which the lead 106 is implanted into the subject's brain. For example, the lip 416 can extend between about 1 mm and about 5 mm below the portion of the housing 408 including the pass-through port 414. The outer diameter of the lip 416 can be substantially the same or slightly less than the inner diameter of the burr hole such that the lip 416 can be press fit into the bur hole by the implanting surgeon.

The pass-through port 414 can be used to stabilize and secure the lead 106. The pass-through port 414 can be used to seal the burr hole. For example, the pass-through port 414 can include a flexible material that includes a slit. The lead 106 can pass-through the slit in the flexible material, which can seal around the lead 106. The sealed flexible material can prevent contaminants from entering the burr hole and can be implemented as an elastomer or polymer, such as a medical grade Silicone. The housing 408 can also include a burr hole cap that can cover and seal the pass-through port 414.

Figure 7A:
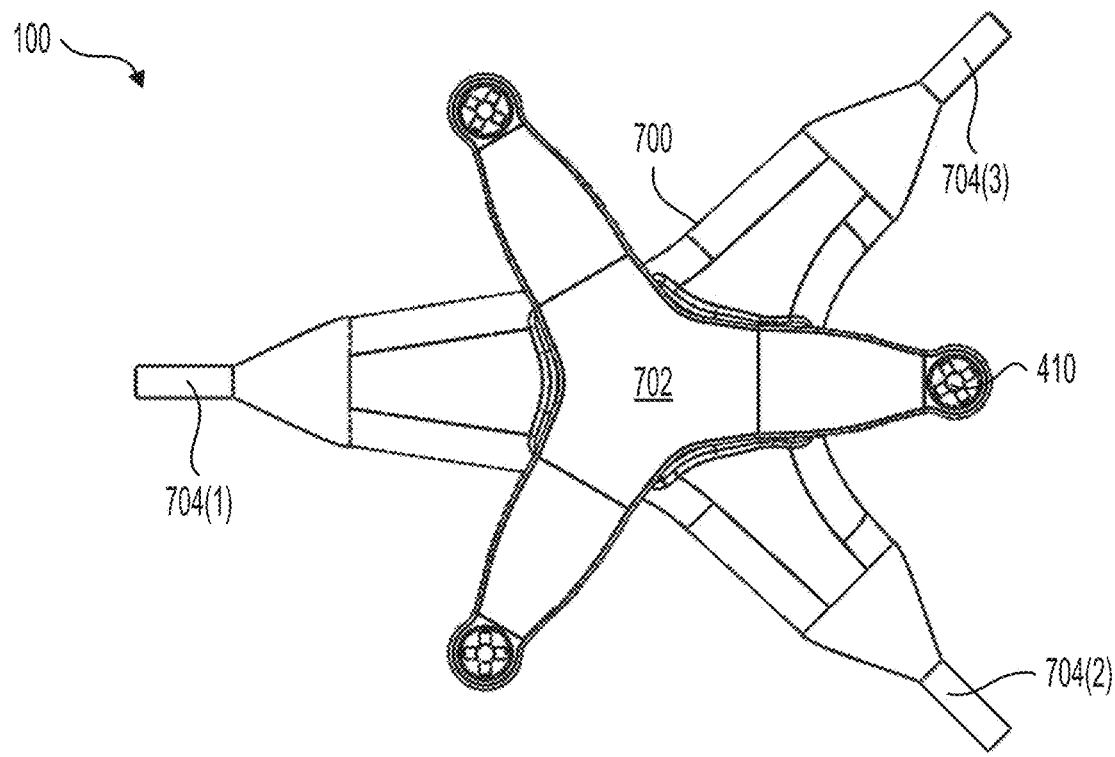
FIGS. 7A and 7B illustrate an example recording patch.
Figure 7B:
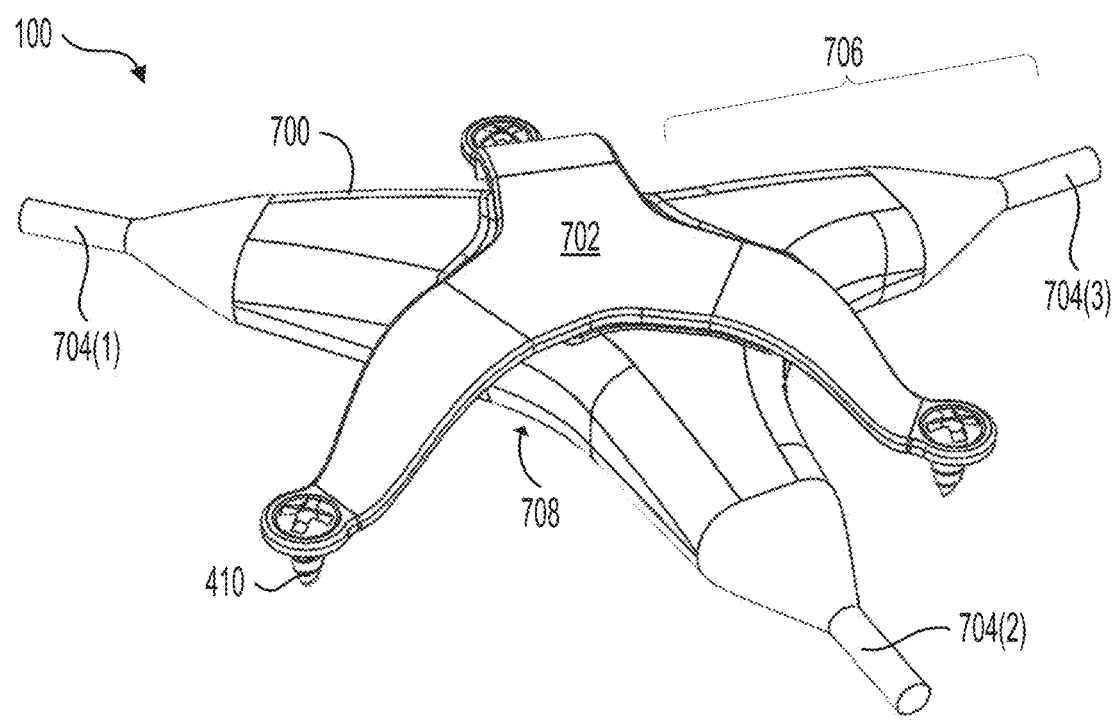

FIGS. 7A and 7B illustrate an example recording patch 100. FIG. 7A illustrates a top view of the recording patch 100. FIG. 7B illustrates a perspective view of the recording patch 100. Referring to FIGS. 7A and 7B together, the recording patch 100 can include a housing 700 that is coupled with the subject's skull via an anchor 702. The housing 700 can include ports 704(1)-704(3), which can be referred to as ports 704.

The components of the recording patch 100 can be enclosed within the housing 700. For example, the housing 700 can house a controller 406 and the antenna 404 as described above in relation to FIG. 6, among others. The housing 700 can be manufactured from plastic or be a hermetically sealed titanium case. The housing 700 can be molded around the components of the recording patch 100. The housing 700 can include one or more electrode sites to enable the housing 700 to be used as a ground or reference for the recordings made at the lead 106. The housing 408 can be metal and the housing 408 itself can be used as a ground or reference electrode.

The housing 700 can be configured in a "radial" or "spoke and hub" configuration. In these configurations, the housing 700 can include a plurality of spokes 706 that radiate out from a central hub 708. Each of the spokes 706 can terminate with or otherwise include at least one port 704. The housing 700 can include between about 2 and about 10, between about 2 and about 8, between about 2 and about 6, or between about 2 and about 4 spokes 706.

The recording patch 100 can include a plurality of spokes 706. Each spoke 706 can include one or more ports 704. Each spoke 706 may include only input ports 704 or only output ports 704, or a combination thereof. Each port can include between about 2 and about 64, between about 2 and about 32, or between about 2 and about 12 contacts to make an electrical connection with the contacts of leads 106 or cables 108. The spokes 706 or a portion thereof can be flexible to enable the recording patch 100 to conform to the shape of the subject's skull. For example, the distal portion of the spokes 706 can include a strain relief that enables flexing at or near the ports 704. The recording patch 100 can include a flexible or mechanical joint at the connection between the spokes 706 and the hub 708 to enable the spokes 706 to deflect and conform to the shape of the subject's skull. The spokes 706 can project from the hub 708 at a predetermined angle to conform to the shape of the subject's skull. The housing 700, from a side profile, can include a convex shape that enables the recording patch 100 to be secure against the subject's skull. The convex shape of the recording patch 100 can substantially match the curvature of the subject's skull. The housing 700 can be flexible to conform to the curvature of the subject's skull.

The recording patch 100 can include a plurality of ports 704. The recording patch 100 can include one or more input ports 704 and one or more output ports 704. The input ports 704 can electrically couple with the pulse generator 102 and the output ports 704 can electrically couple with the leads 106. For example, a port 704 can receive a connection from the cable 108. The ports 704 can be similar to the ports 400 described above in relation to FIG. 4. For example, the ports 704 can each include connections 402 that make electrical contact with the contacts of the lead 106 or the cable 108. The ports 704 can include one or more screws 410 to secure a cable 108, cable to a lead 106, or other cable to the ports 704.

The output ports 704 can electrically couple with a lead 106. The ports 704 (both the input or output ports 704) can be female or male ports. For example, the input port 704 can be a female port and the output ports 704 can be male ports. The output ports 704 can include a cable tether. The cable tether can include a connector to couple the lead 106 with the recording patch 100. The leads 106 can be permanently coupled with the output ports 704. For example, a cable can extend from the ports 704. The distal end of the cable can include the lead 106. The lead 106 can be permanently coupled with an output port 704 when the cable or port 704 does not include a connector that enables the lead 106 to be disconnected form the recording patch 100.

Figure 8:
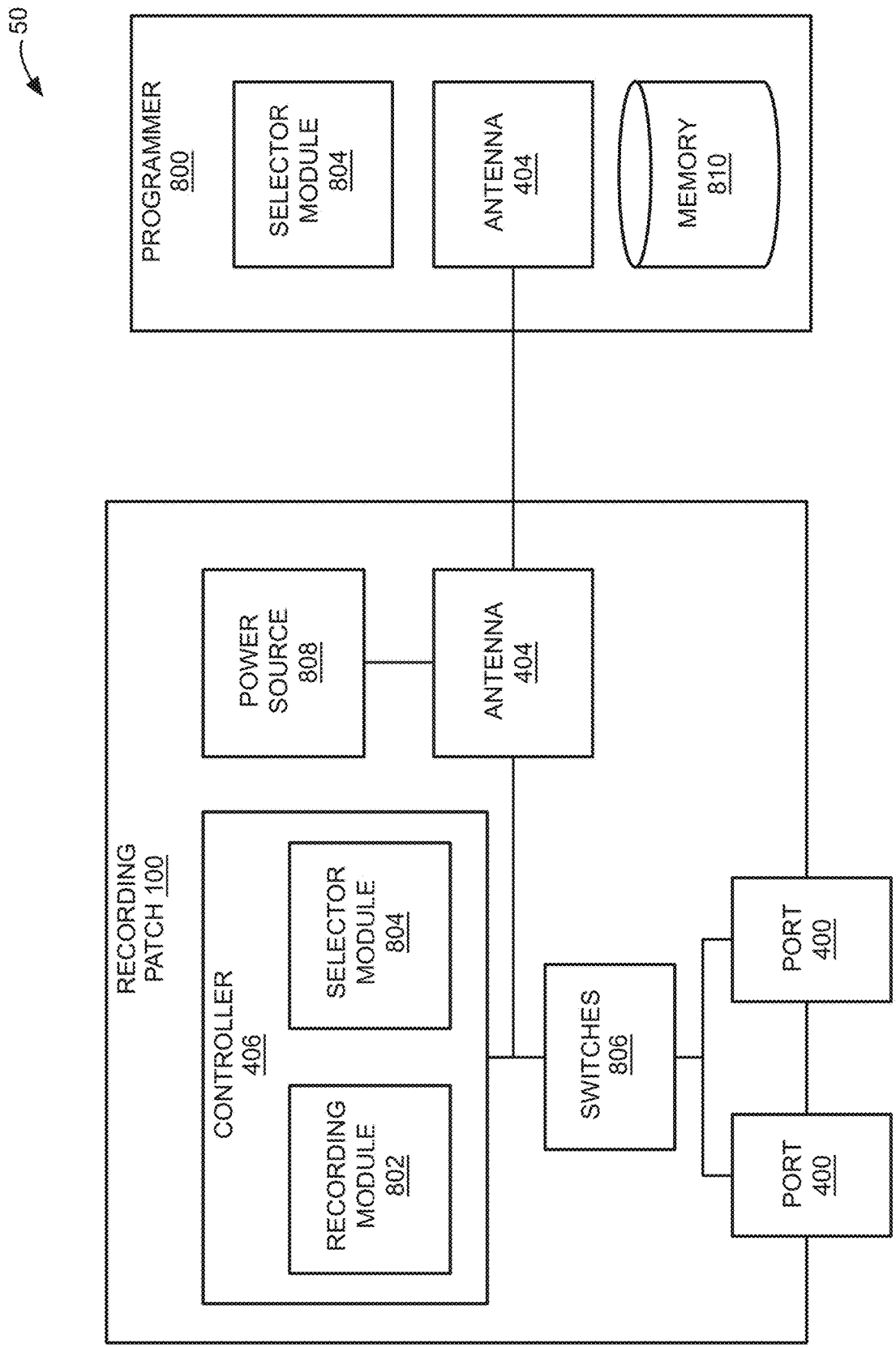
FIG. 8 illustrates a block diagram of an example schematic of the system illustrated in FIGS. 1-3.

The recording patch 100, as illustrated in FIGS. 7A and 7B can include an anchor 702. The anchor 702 can be a component that separates from the housing 700. For example, the anchor 702 can be a separate bracket that a medical professional can use to couple the recording patch 100 to the subject's skull. The anchor 702 can be an integral portion of the housing 700. For example, the anchor 702 cannot be separated from the housing 700. The anchor 702 can include a plurality of arms 710. The arms 710 can extend between each of the spokes 706. The arms 710 can terminate with an anchor point. The anchor point can be an opening or hole to receive a screw 410. A screw 410 can be placed through each of the anchor points and screwed into the subject's skull to couple the recording patch 100 to the subject's skull. The anchor 702 can include a medical grade metal, such as stainless steel or titanium FIG. 8 illustrates a block diagram of an example schematic of the system 50. The system 50 can include the recording patch 100 and a programmer 700, which can be more generally referred to as an external source or a transmitter and receiver. The recording patch 100 can include the controller 406, which can include a recording module 702 and a selector module 704. The recording patch 100 can include switches 706 that can interconnect the controller 406 and ports 400. The recording patch 100 can include a power source 708 and the antenna 404. The system 50 can include the programmer 700. The programmer 700 can include an instance of the selector module 704, an antenna 404, and a memory element 710. The recording patch 100 can include the controller 406. The controller 406 can include the recording module 702. The recording module 702 can include a plurality of amplifiers. For example, the recording module 702 can include an amplifier for each of the lead's channels.

The controller 406 can be an application specific integrated circuit (ASIC). Each of the electronic components of the recording patch 100 can be components of the controller 406. For example, the switches 706, the antenna 404, and the power source 708 can each be components of controllers ASIC. The controller 406 and components of the recording patch 100 can be divided among a plurality of ASICs.

The recording module 702 can pass the incoming signals from the lead 106 through its amplifiers to generate amplified signals based on the incoming signals. The amplifiers can have a gain between about 50 times to 5000 times, or between about 60 dB-120 dB. The recording module 702 can digitize the amplified signals. The recording module 702 can digitize the signals at a rate of between about 10 Hz and about 2000 Hz, between about 50 Hz and about 1000 Hz, or between about 50 Hz and about 20,000 Hz. The recording module 702 can perform pre-processing on the original or amplified signal. The pre-processing can include applying low, high, or band pass filters. For example, the recording module 702 can band pass the original signal to remove electrical noise. The recording module 702 can band pass filter the signals to remove all but desired frequency ranges or bands. For example, the recording module 702 can filter the signals to remove frequencies in the signals above about 100 Hz, 250 Hz, or about 500 Hz.

The recording module 702 can communicate with the programmer 700 via the antenna 404. The recording module 702 can transmit the amplified signal to the programmer 700 via the antenna 404. The controller 406 can include the selector module 704. The recording patch 100 and the programmer 700 can each include instances of the selector module 704. In some examples, only one of the recording patch 100 or the programmer 700 include an instance of the selector module 704. For example, only the programmer 700 may include an instance of the selector module 704 and the recording patch 100 can transmit data (e.g., electrical signals) to the programmer 700 for analysis.

The selector module 704 can select one or more electrodes of the lead 106 over which a stimulation signal is delivered to the subject. The selector module 704 can select the electrodes to use for stimulation based on the signal characteristics of the signals received from the lead 106. The characteristics can be the amount of power in a beta band of the received signals. The beta band can be between about 10 Hz and about 30 Hz, for example. The selector module 704 can select the electrodes that include the most power in the beta band as the electrodes to use for stimulation. The selector module 704 can select the electrode with the highest amount of power in the beta band as a stimulating electrode. The selector module 704 can select the electrodes having power in the beta band over a predetermined threshold as the stimulating electrodes. In some implementations, the electrode with the most power in the beta band can be selected. If a plurality of electrodes have power in the beta band, each of the plurality of electrodes can be selected as a multitude.

If a multitude of electrodes is selected they may stimulate at the same signal amplitude, or at different signal amplitudes. If at different signal amplitudes, the individual single amplitudes applied to each electrode may be chosen to be proportional to the power of beta band detected. For example, if two electrodes display beta band power upon recording, with a first electrode demonstrating twice as much power as a second electrode, the signal amplitude for each electrode would be chosen such that the first electrode would have a signal amplitude twice as that of the second electrodes. In another use scenario, the signal amplitude could be applied between two or more electrodes that have each demonstrated beta band power.

The recording patch 100 can include a plurality of switches 706. The switches 706 can be components of the controller 406. The switches 706 can selectively interconnect the connections in the port 400 leading to the pulse stimulator 102 to the connections in the port 400 leading to the lead 106. The switches 706 can selectively interconnect the connections in the port 400 leading to the lead 106 to the recording module 702. Selectively interconnecting, via the switches 706, can include connecting any of a port's connections to any input pins of the controller 406 or other connections of another port 400. In some implementations, the switches can be implemented as mechanical relays, micromechanical MEMS relays, electrical switches such as JFET, MOSFET, or other FET technology, or other microfabrication technology. In some embodiments, no switches are necessary, but a high impedance input to the recording module would be required. From this input a recording signal with high signal to noise can be captured, but stimulation signal from the pulse generator 102 would not sink.

The controller 406 can control the switches 706 to put the recording patch 100 into a recording mode or a pass-through mode. For example, the controller 406 can control the opened or closed state of the switches 706. During a pass-through mode, the switches 706 can couple the connections of a first port 400 with the connections of a second port 400. The pass-through mode can enable stimulation signals from the pulse stimulator 102 to pass through the recording patch 100 and to the lead 106 without substantial alteration at the recording patch 100.

During a recording mode, the switches 706 can couple the connections of the port 400 coupled with the lead 106 with the controller 406. The switches 706 can couple each of the lead's electrodes with the controller 406 or only a portion thereof.

The recording patch 100 can include a power source 708. The power source 708 can be a rechargeable battery. The power source 708 can include a super capacitor. The power source 708 can be recharged wirelessly via the programmer 700. For example, the antenna 404 of the programmer 700 and the recording patch 100 can inductively couple to provide the recording patch 100 with power. The power can be passed to the power source 708 to charge the power source 708.

The programmer 700 can be an external data processing system. The programmer 700 can be a stand-alone device. The programmer 700 can be a mobile device such as a laptop, tablet, or smart phone. The programmer 700 can read and write data to the recording patch 100 through wireless communication with the recording patch 100 using the antennas 404. For example, the programmer 700 can receive and store digitized biological signals from the recording patch 100. The programmer 700 can transmit configuration information, such as which connections of the ports to interconnect, to the recording patch 100.

The programmer 700 can include a screen to provide visual information to the user. The information can include readouts of the electrical signals received at each of the lead's electrodes, power within specified bands (e.g., the beta band) of the signals, or settings (e.g., which electrodes are configured as stimulation electrodes). The screen can be a touch screen. The programmer 700 can include an antenna 404 that can be inductively coupled with the antenna 404 of the recording patch 100 to transmit data and power to between the devices. Via the screen the selector module 704 can display one or more characteristics of the received signals. Via the screen the selector module 704 can display plots of power within, for example, the beta band. Via the screen the selector module 704 can display indications or approximations of the signals' characteristics. For example, the selector module 704 can indicate whether a given channel has a "low," "medium," or "high" level of power in the beta band.

The programmer 700 can include an antenna 404. The antenna 404 of the programmer 700 can have a diameter that provides efficient communication with the patch 100 via the antenna 404 of the patch 100. For example, the antenna 404 of the programmer 700 can have a diameter between about 25 mm and about 75 mm or between about 45 mm and about 55 mm while the antenna 404 of the patch 100 can have a diameter between about 15 mm and about 35 mm or between about 20 mm and about 30 mm. The programmer 700 can communicate with the patch 100 wirelessly after the implantation of the patch 100. The programmer 700 can send data to the patch 100 in order to set the recording parameters that the patch 100 uses to record electrical signals via the lead 106. For example, the programmer 700 can set which electrodes are used for the recording and the sampling frequency that is used to make the recording.

The programmer 700 can download data (e.g., usage data, recorded physiological data, or device configuration information) from the patch 100. The programmer 700 can receive the data from the patch 100 in substantially real time (e.g., the data can be streamed to the programmer 700 from the patch 100). The patch 100 can transmit the data to the programmer 700 in batches. For example, the patch 100 can include an on-board memory to which the recordings from the lead 106 are stored and then downloaded or transmitted to the programmer 700. Once received by the programmer 700, the programmer 700 can store the data on the memory 710. A user can later download the recording data from the memory 710 to a data processing system for analysis. The programmer 700 can perform all or portions of analysis performed by the data processing system.

The programmer 700 can be used to recharge the internal batteries of the patch 100. For example, the antenna 404 of the programmer 700 can be used to inductively couple power from an external power source to the patch 100. In some implementations, the patch 100 can have no internal power source and inductive power from the programmer 700 can be used to power the patch 100.

The programmer 700 can include an instance of the selector module 704. The programmer's selector module 704 can perform any of the functions performed by the recording path's selector module 704. For example, the selector module 704 can calculate characteristics of the signals detected by the leads 106 and select one or more electrodes of the lead 106 over which a stimulation signal is delivered to the subject. The selector module 704 can select the electrodes to use for stimulation based on the signal characteristics of the signals received from the lead 106. The characteristics can be the amount of power in a beta band of the received signals. The beta band can be between about 10 Hz and about 30 Hz, for example. The selector module 704 can select the electrodes that include the most power in the beta band as the electrodes to use for stimulation. The selector module 704 can select the electrode with the highest amount of power in the beta band as a stimulating electrode. The selector module 704 can select the electrodes having power in the beta band over a predetermined threshold as the stimulating electrodes.

Figure 9A:
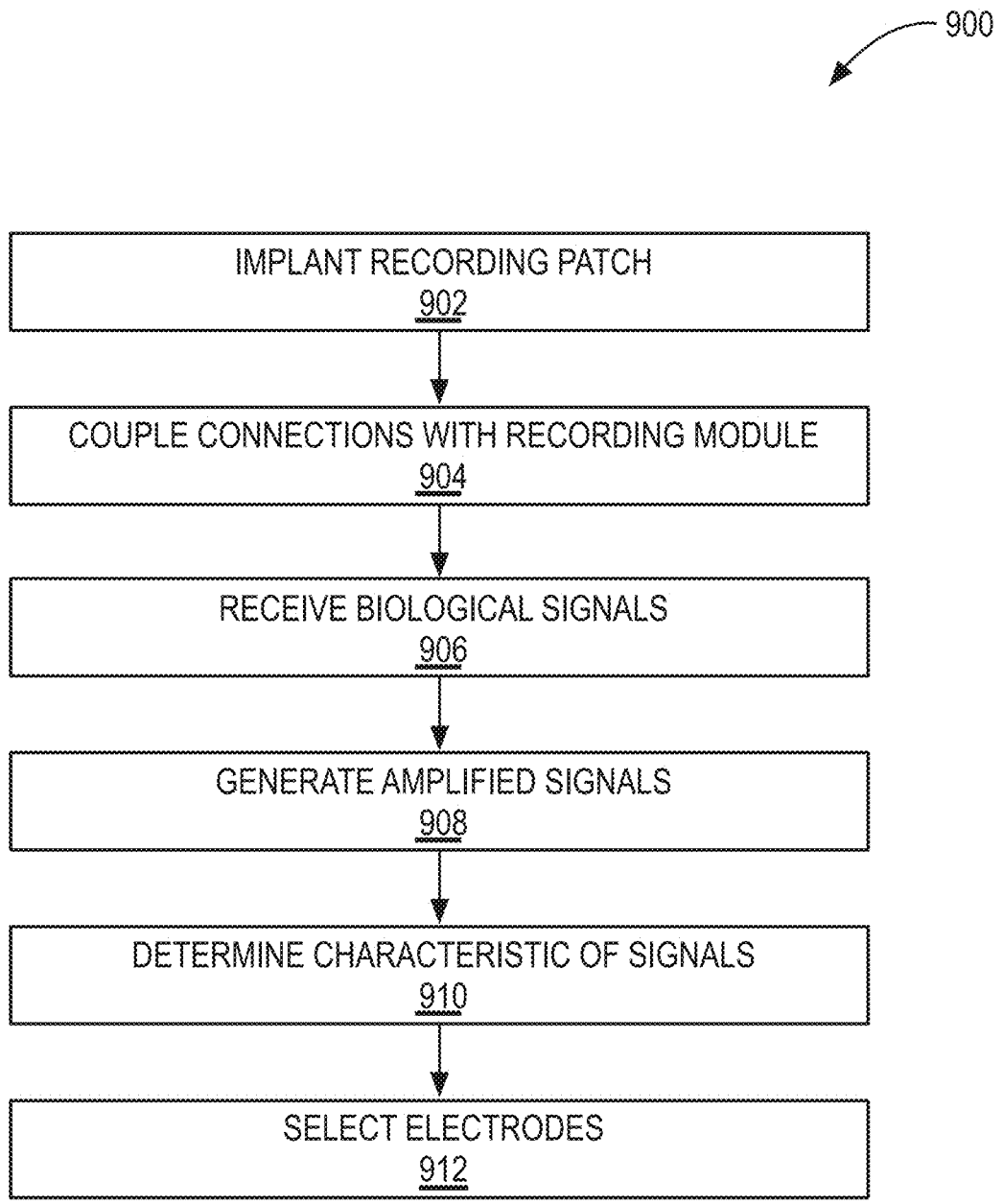
FIGS. 9A and 9B illustrate block diagrams example methods to record biological signals with the system described herein.

FIG. 9A illustrates a block diagram of an example method 900 to record biological signals. The method 900 can include implanting a recording patch (ACT 902). The method 900 can include coupling a plurality of connections with a recording module (ACT 904). The method 900 can include receiving biological signals (ACT 906) and generating amplified signals (ACT 908). The method 900 can include determining characteristics of the signals (ACT 910). The method 900 can include selecting electrodes (ACT 912).

The method 900 can include implanting a recording patch (ACT 902). The recording patch can be any of the recording patches described herein. The recording patch can be implanted into a subject. The recording patch can include a first port that is configured to receive a connection from an implantable pulse stimulator. The first port can include a first plurality of connections. The recording patch can include a second port that can be configured to receive a connection from an implantable lead that is implanted into the subject. The lead can include a plurality of electrodes. The second port can include a second plurality of connections. The recording patch can include a plurality of switches that can be in electrical communication with the first plurality of connections and the second plurality of connections. The recording patch can include a recording module that is executed by one or more processors of the recording patch. The recording patch can include an instance of a selector module.

The recording patch can be implanted beneath the subject's scalp following the implantation of one or more leads into the subject's brain. The leads can include a plurality of electrodes. The lead can include a plurality of electrodes positioned around the circumference of the lead at plurality of different axial locations. For example, at a plurality of different axial locations along the body of the lead's body, the lead can include an electrode at 0, 120, and 240 degrees. The lead can be implanted such that the lead's electrodes are positioned within the subject's subthalamic nucleus.

The method 900 can include coupling a plurality of connections with a recording module (ACT 904). The patch 100 can include a first and a second port. One port can be coupled with an implanted lead and be referred to as a lead port and one port can be coupled with an implanted stimulator and be referred to as a stimulator port. At a first time point after the implantation of the recording patch, the recording patch can wirelessly receive instructions that place the recording patch in a recording mode. In the recording mode, the recording patch's switches can couple one or more of the lead port's connections to the recording module. During the recording mode, the recording patch can inductively couple with a programmer or other external source to wirelessly receive power that powers the recording patch.

At a second time point before or after the recording patch collects recordings of biological signals from the subject, the recording patch can receive instructions can cause the recording patch to configure one or more of the switches in a pass-through configuration such that the switches couple connections of the lead port with connections of the stimulator port. In a pass-through configuration, the connections between the first port and the second port can bypass the recording module and stimulation signals can be delivered to the subject prior to or after the recording phase.

The method 900 can include receiving biological signals (ACT 906). During the recording mode, the recording patch can receive biological signals. The recording patch can receive the biological signals via the one or more electrodes that are connected to the lead port's connections to pass the biological signals to the recording module. The biological signals can be electrical activity generated by the brain or other neurological tissue. For example, the biological signals can be LFPs.

The subject can perform physical acts during the receiving and recording of the biological signals. For example, the subject can perform one or more of, but not limited to, the following acts on one side or both sides of the body simultaneously: general movement, rest entire body, moving upper limbs, moving fingers, moving wrists, moving elbows, moving lower limbs, moving toes, moving ankles, moving knees, moving thighs, moving hips, moving extremities, moving head, moving neck, talking, clearing throat, swallowing, coughing, and speaking.

The method can include generating amplified signals (ACT 908). The patch can include one or more amplifies. The patch can pass the biological signals through the amplifies to generate amplified signals. The amplifiers can have a gain of between about 50 and about 5000× or between about 60 dB and about 120 db. The recording patch can sample the biological signals at between about 1 kHz and about 32 kHz, between about 8 kHz and about 32 kHz, between about 12 kHz and about 32 kHz, or between about 24 kHz and about 32 kHz.

The recording patch can perform pre-processing on the biological signals or the amplified signals. The pre-processing can include band pass filtering, high or low pass filtering, smoothing, down sampling, up sampling, or a combination thereof. For example, the signals can be band pass with a filter having a pass band between about 5 Hz and about 5 kHz. The pre-processing can include applying a notch filter (at about 50 Hz or about 60 Hz) to remove power-line noise. The recording patch can perform the pre-processing digitally once the biological signals are digitized by the recording module or by one or more analog filters that can process the biological signals prior to the digitization of the biological signals.

The method 900 can include determining characteristics of the signals (ACT 910). The characteristics of the signals can be determined by the recording patch's recording module or selector module. The recording patch's controller can determine the characteristics of the biological signals or the amplified signals. The recording patch can also wirelessly transmit the amplified signal to an external device (e.g., a programmer or other device) that can determine the characteristic of the signals. An instance of the selector module executed by the recording patch and an instance of the selector module executed by a programmer can cooperatively work to determine the characteristics of the signals. For example, the recording patch can perform pre-processing and filtering and then the programmer's instance of the selector module can determine the power within the beta band of the signals.

The characteristic of the signals can be a power level in a beta band of each of the amplified biological signals. The recording patch or the external device can divide the amplified biological signals into a plurality of segments. For example, the biological signals can be divided into 15 second segments. The power in each segment can be calculated using the Welch method using a 1 second Hanning window with a frequency resolution of 1 Hz. The power of different frequency bands can be calculated as the area under curve of the power spectral density curves. For example, the recordings can be divided into a plurality of bands, such as alpha (7.5-12 Hz), low beta (12.5-16 Hz), medium beta (16.5-20 Hz) and high beta (20.5-30 Hz).

The method 900 can include selecting electrodes (ACT 912). The method 900 can include selecting an electrode of the plurality of electrodes based on the at least one signal characteristic of the biological signal. For example, the controller or the programmer can select each of the electrodes that received a biological signal having a power in the beta band above a predetermined threshold. The controller or the programmer can select the electrode that received a biological signal having the highest power in the beta band. The one or more selected electrodes can be used as stimulating electrodes. The selector module can select the electrode at each axial position with the highest power in the beta band. In some implementations, the selector module can select a plurality of electrodes. For example, the selector module can select the plurality of electrodes with the two, three, etc highest level of power in the beta band.

At a time point after the stimulating electrodes are selected, the recording patch can connect the implantable pulse stimulator to the selected electrodes. For example, the connections electrically coupled with the pulse stimulator can be coupled with the connections at the lead port that are in electrical communication with the selected electrodes. The recording patch can place the switches in a pass-through configuration such that the switches couple the connections of the two ports together while bypassing the controller.

When in the pass-through configuration, the pulse stimulator can generate a stimulation signal that is transmitted to the selected leads via the recording patch. Once the patch is configured into the pass-through configuration, the external power supply from the recording patch can be removed. The external power supply can be removed prior to transmitting the stimulation signal to the electrodes selected as stimulation electrodes. The acts of the method 900 can be repeated at predetermined time points or intervals. For example, during doctor visits the physician can place the recording patch into a recording mode to retrieve electrical signals from each of the electrodes and the selector modules can re-determine which of the electrodes are receiving electrical signals with the highest power in the beta band. During different iterations of the method 900, different electrodes can be selected as stimulating electrodes. For example, during a first iteration of the method 900 a first plurality of the electrodes can be selected as stimulation electrodes. At another time point during a second iteration of the method 900 a second plurality of electrodes (which can be a subset of the first plurality of electrodes or a different plurality of electrodes) can be selected and coupled with the recording module.

Figure 9B:
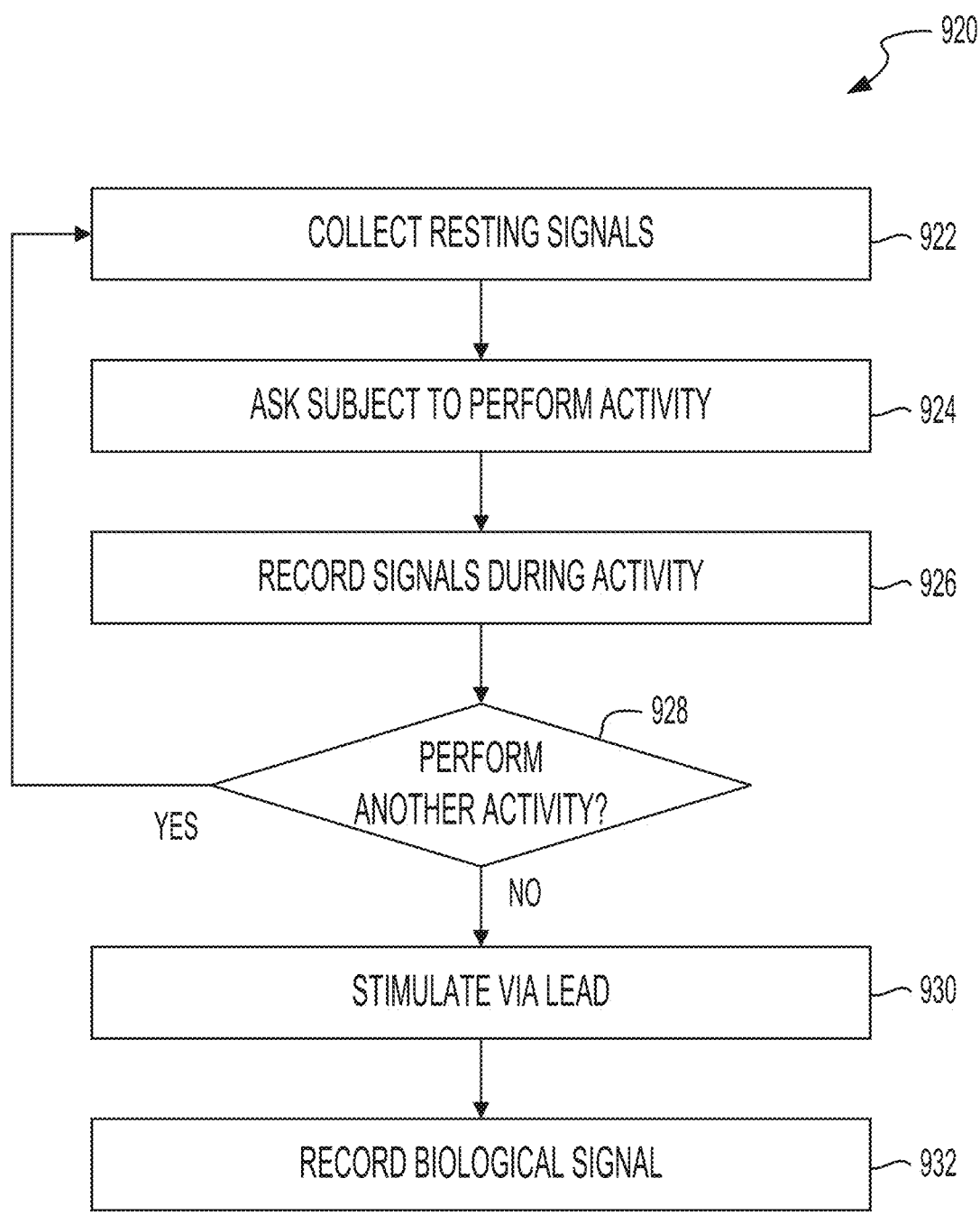

FIG. 9B illustrates a block diagram of an example method 920 to receive biological signals. The method 920 can be used in conjunction with the ACTs of the method 900. For example, the method 920 can be used at ACT 908 of the method 900. The method 920 can include collecting resting signals (ACT 922). The method 920 can include asking a subject to perform an action (ACT 924). The method 920 can include collecting signals during the action (ACT 926). The method 920 can include determining whether the subject should perform another activity (ACT 928). The method can include stimulating the subject (ACT 930). The method 920 can include receiving biological signals (ACT 932).

As set forth above, the method 920 can include collecting resting signals (ACT 922). The signals can be biological signals. For example, the biological signals can be electrical activity generate by brain or other neurological tissue. For example, the biological signals can be LFPs. The subject can be asked to relax or otherwise not move as the resting signals are collected. For example, the subject can be asked to recline, sit, or lie down as the recording patch collects the signals. To record the signals, the programmer can set the recording patch to the recording mode. The recording patch can receive the biological signals via the one or more electrodes of the lead. The recording patch can collect or otherwise record the resting signals as the subject rests (e.g., does not substantially move). The recording patch can collect the resting signals at a predetermined time interval after the subject begins to rest. For example, the subject can be asked to recline and the recording patch can begin to collect the resting signals about 1 minute, 5 minute, 10 minutes, or 15 minutes after the subject begins to recline.

The method 920 can include asking the subject to perform an activity (ACT 924). A medical professional can request that the subject perform an activity or action when prompted by the programmer. The activity can include moving certain parts of the body, walking, turning, standing, coughing, speaking, throat clearing, swallowing, blinking, winking, squinting, performing hand gestures, performing finger gestures, performing elbow movements, performing shoulder movements, breathing, or halting the breath, among others. The medical professional can ask the subject to physically perform the activity or the medical professional can ask the subject to visualize or imagine performing the activity.

The method 920 can include collecting signals during the activity (ACT 926). The signals can be biological signal as described above in relation to ACT 922. The biological signal can be collected as the subject performs (physically or mentally) the activity of ACT 924. The signals can be recorded immediately following the completion of activity. For example, the recording patch can record the signals 1 min, 5 min, 10 min, 15 min, or 30 min after the completion of the activity. The biological signals recorded at ACT 922 and ACT 926 can be continuously recorded during a testing session. For example, the recording patch can be placed into a recording mode prior to the medical professional asking the subject to rest and then continue recording through the ACTS of the method 920. The medical professional or the programmer can annotate the recorded signal to indicate the transitions between different phases of the testing session. For example, via the programmer, the medical professional can indicate when the subject begins to rest and when the subject begins or ends the activity. The programmer can record the time of the indication or can set a flag in the recorded signal to indicate each of the transitions.

The method 920 can include determining whether to test another activity (ACT 928). The programmer can be loaded with testing policy that can indicate the one or more activities that the subject should perform during the method 920. A medical professional can select or configure the activities stored in the testing policy. The programmer can determine whether there are additional activities to ask the subject to perform. If there are additional activities to perform, the method 920 can return to the ACT 922. For example, determining there are additional activities to perform, the programmer can display a message to the medical professional to request that the medical professional ask the subject to rest. After the recording patch records additional resting signals (e.g., repeats ACT 922), the programmer can request that the medical professional instruct the subject to perform the next activity listed in the testing policy (e.g., repeats ACT 924). The recording patch can collect the signal during or after the subject completes the next activity listed in the testing policy (e.g., repeats ACT 926). The method 920 can include repeating the ACTs 922-926 until the programmer determines there are no more additional activities in the testing policy for the subject to perform.

The method 920 can include stimulating the subject via the lead (ACT 930). Also referring to FIG. 1, among others, the programmer can send an instruction to the recording patch to place the recording patch in a pass-through mode, such that electrical stimulations from the pulse stimulator 102 can pass from the pulse stimulator 102 to the lead 106. As described above, the lead 106 can include a plurality of electrodes. The pulse stimulator 102 can individually address each of the plurality of electrodes. The programmer can select one or more of the plurality of electrodes to which the stimulation should be delivered from the pulse stimulator 102. For example, the pulse stimulator 102 can include a plurality of internal switches that can be opened or closed to electrically disconnect or connect, respectively, an electrode from a stimulation source of the pulse stimulator 102. The pulse stimulator 102 can deliver the stimulation single to one electrode, a plurality of electrodes, or all of the electrodes of the lead 106.

The method 920 can include receiving biological signals (ACT 932). To receive biological signals, the programmer can place the recording patch back into the recoding mode. The recording patch can receive the biological signals via the one or more electrodes that are connected to the lead port's connections to pass the biological signals to the recording module. The biological signals can be electrical activity generate by brain or other neurological tissue. For example, the biological signals can be LFPs. The recording patch can receive or otherwise record the biological signal starting at the completion of the stimulation signal delivered at ACT 930. The recording patch can continue to record the biological signals for between about 1 min and about 30 min, between about 1 min and about 20 min, or between about 1 min and about 15 minutes following the completion of the stimulation signal. The ACT 930 and the ACT 932 can be repeated a plurality of times. For example, the ACT 930 and ACT 932 can be repeated for each electrode of the leads 106.

The method 920 can include determining characteristics of the recorded signal at different time points. For example, the characteristics of the biological signal post-stimulation or post-activity can be compared to the characteristics of the biological signal recording during ACT 922 when the subject was at rest. The characteristics of the signals can be determined by the recording patch's recording module or selector module. The recording patch's controller can determine the characteristics of the biological signals. Determining the characteristics is further described in relation to FIGS. 10-14, among others. The recording patch can also wirelessly transmit the amplified signal to an external device (e.g., a programmer or other device) that can determine the characteristic of the signals. An instance of the selector module executed by the recording patch and an instance of the selector module executed by a programmer can cooperatively work to determine the characteristics of the signals. For example, the recording patch can perform pre-processing and filtering and then the programmer's instance of the selector module can determine the power within the beta band of the signals. The characteristic of the recorded signal can be the amount of power in a beta-band of the recorded signal. For example, the recording patch's controller can determine the change in the amount of power in the beta-band between the resting phase (e.g., during ACT 922) and the amount of power in the beta-band after the stimulation signal is provided to the subject (e.g., during ACT 932).

Figure 10:
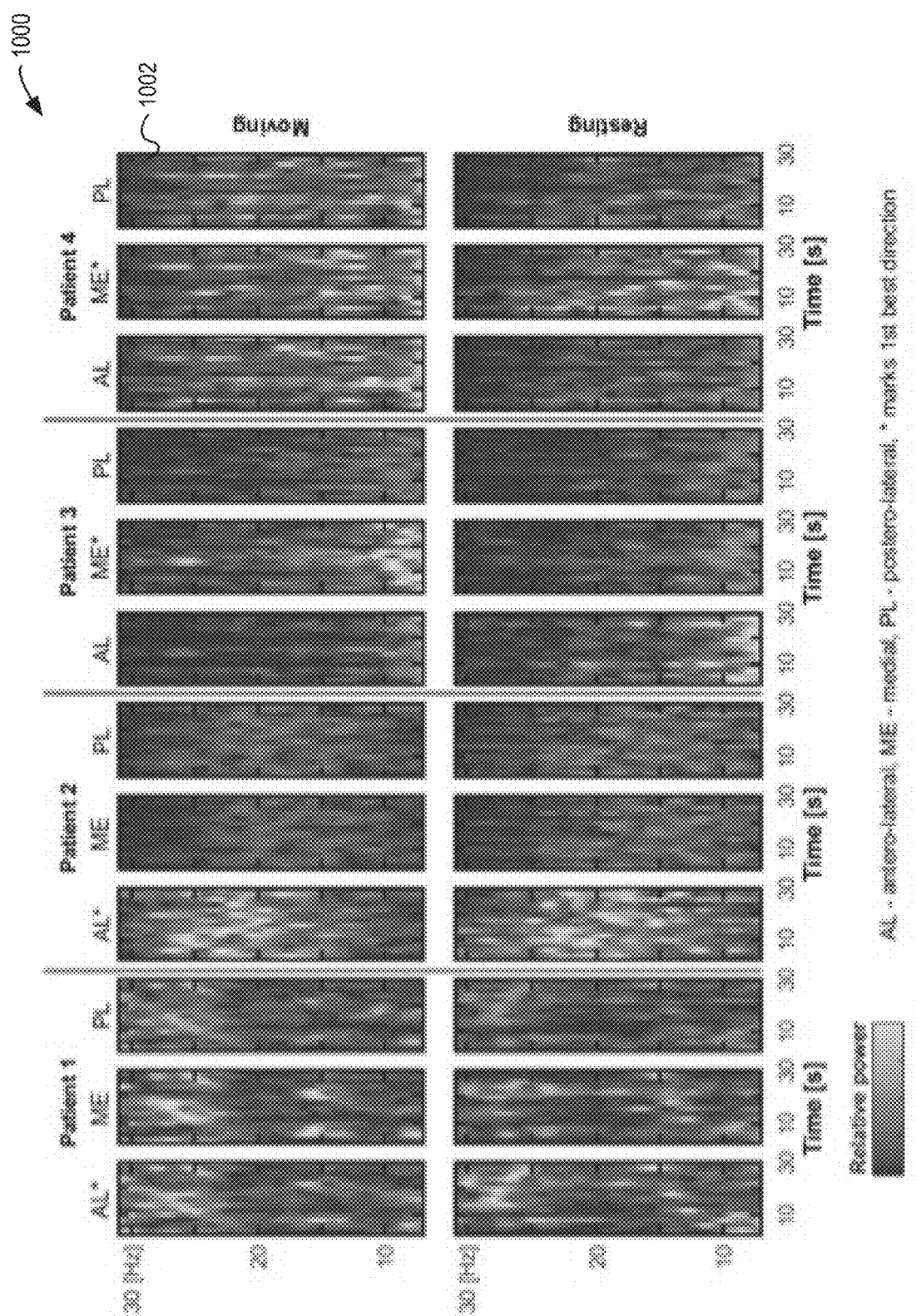
FIGS. 10-13 illustrate plots of the power spectral densities of signals recorded with the systems described herein.

FIGS. 10-13 illustrate the results of recordings made with a system similar to that described herein. FIG. 10 illustrates a plot 1000 of a plurality of power spectral densities 1002. Each of the power spectral densities 1002 was generated from 30-second recordings for both moving conditions (top row) and resting conditions (bottom row). Each recording was split into fifteen two-second epochs to examine changes in power spectral densities over time. Across the conditions and subjects, no marked change was observed over time. Differences were primarily observed between subjects in terms of peak frequency (e.g., the frequency component with most signal energy) and in terms of directions. For example, for subject 1 during moving, peak power was concentrated between about 25 and about 30 Hz. Subject 2 showed peak power during moving and resting between frequencies about 17 and about 27 Hz. For subject 3, peak power was concentrated in a narrow band around 8 Hz. Subject 4 had peak spectral densities between about 8 and about 15 Hz.

Figure 11:
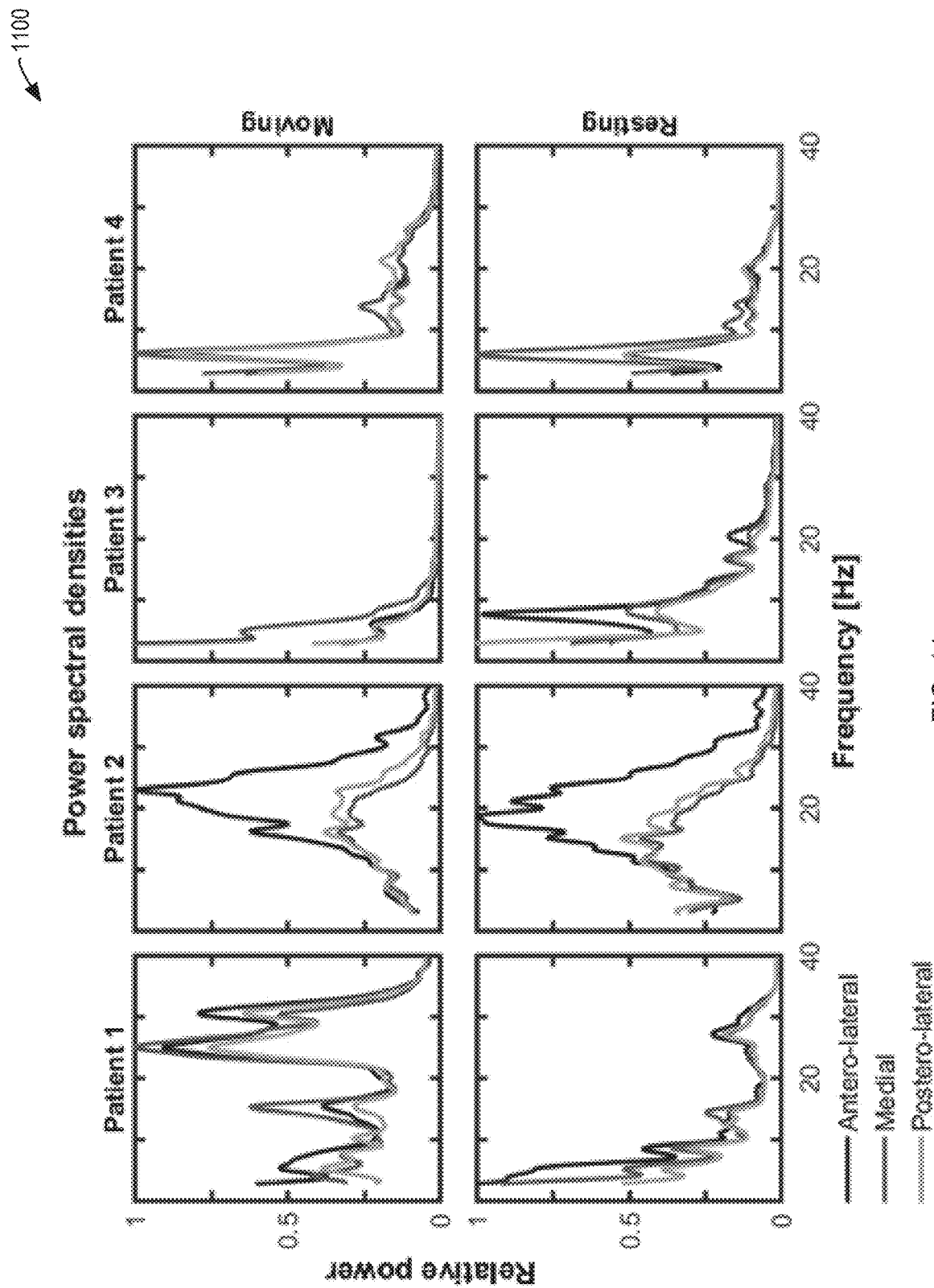

FIG. 11 illustrates a plot 1100 of power spectral densities for each of four subjects. The plot 1100 includes separate power spectral densities form the different lead electrodes pointed in the antero-lateral, medial, and postero-lateral directions. The plot 1100 illustrates that the four subjects experienced directional difference. For example, during moving, subject 1 had peak power in the antero-lateral and medial directions with slightly less power in the postero-lateral direction. Subject 2 showed peak power in the antero-lateral direction with visibly more power than in the medial or postero-lateral direction. During moving, subject 3 had most power in the medial direction. Subject 4 had increased power below 10 Hz in all three directions during moving, but concentrated spectral power in the medial direction during resting.

During resting, the power spectral densities showed more directional differences than during moving. For example, subjects 1, 2, and 3 had heightened activity in the antero-lateral direction with peak power at 27 Hz, 22 Hz and 9 Hz, respectively. Subject 4 showed increased activity at 10 Hz in the medial direction.

The power spectral densities were stored as ranked stimulation directions (e.g., 1st, 2nd, and 3rd best direction) and split the power spectral densities into four frequency bands (e.g., alpha, low beta, medium beta, and high beta). The directions were ranked from the highest beta activity to the lowest beta activity.

Figure 12:
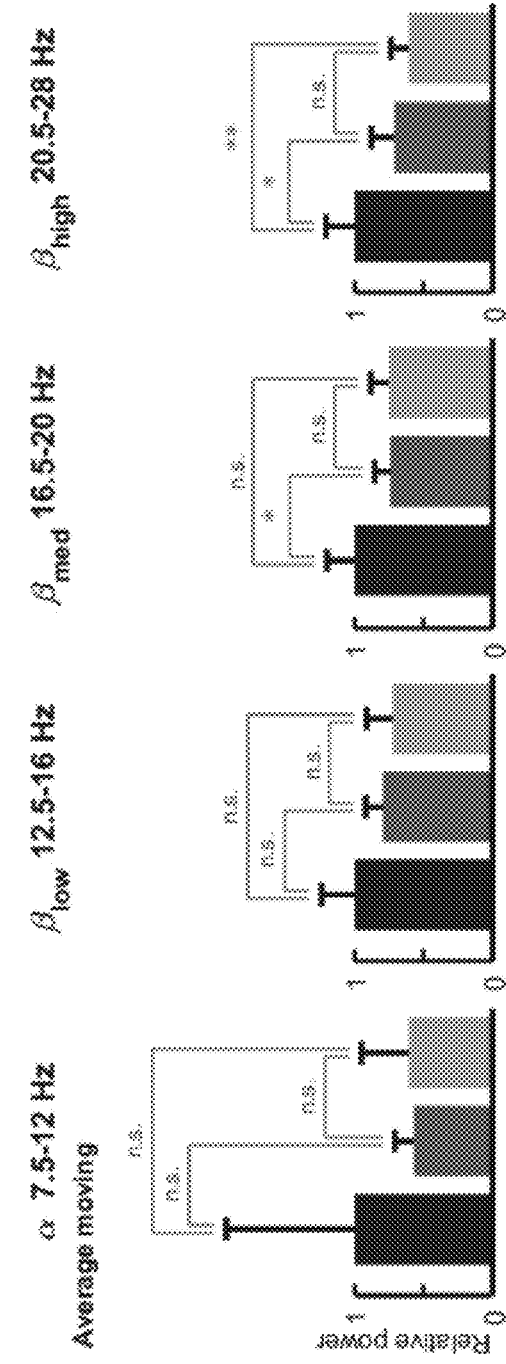
Figure 12:
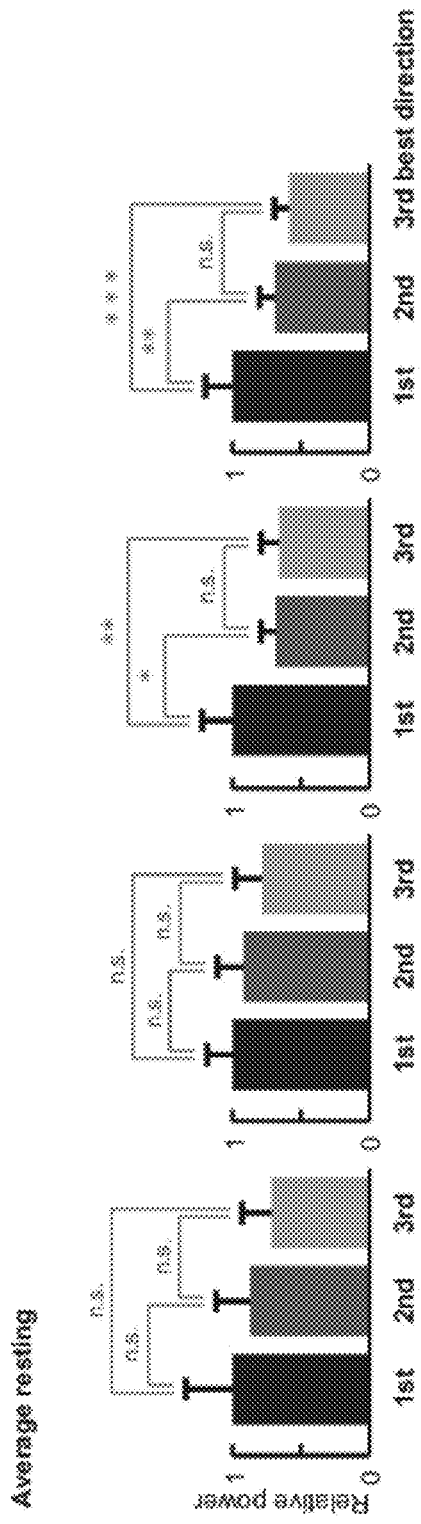

FIG. 12 illustrates a plot 1200 comparing different frequency bands to different stimulation directions. In each of the six plotted examples, the 1st best direction had more power than the 2nd and 3rd best directions. However, in half of the cases these directional differences between directions were not significant. For instance, no significant difference was observed in the alpha frequency band or in the low beta frequency band during moving and resting. Significant differences were detected in the medium and high beta frequency bands and were more pronounced in the high beta frequency band and was particularly marked during resting.

Figure 13:
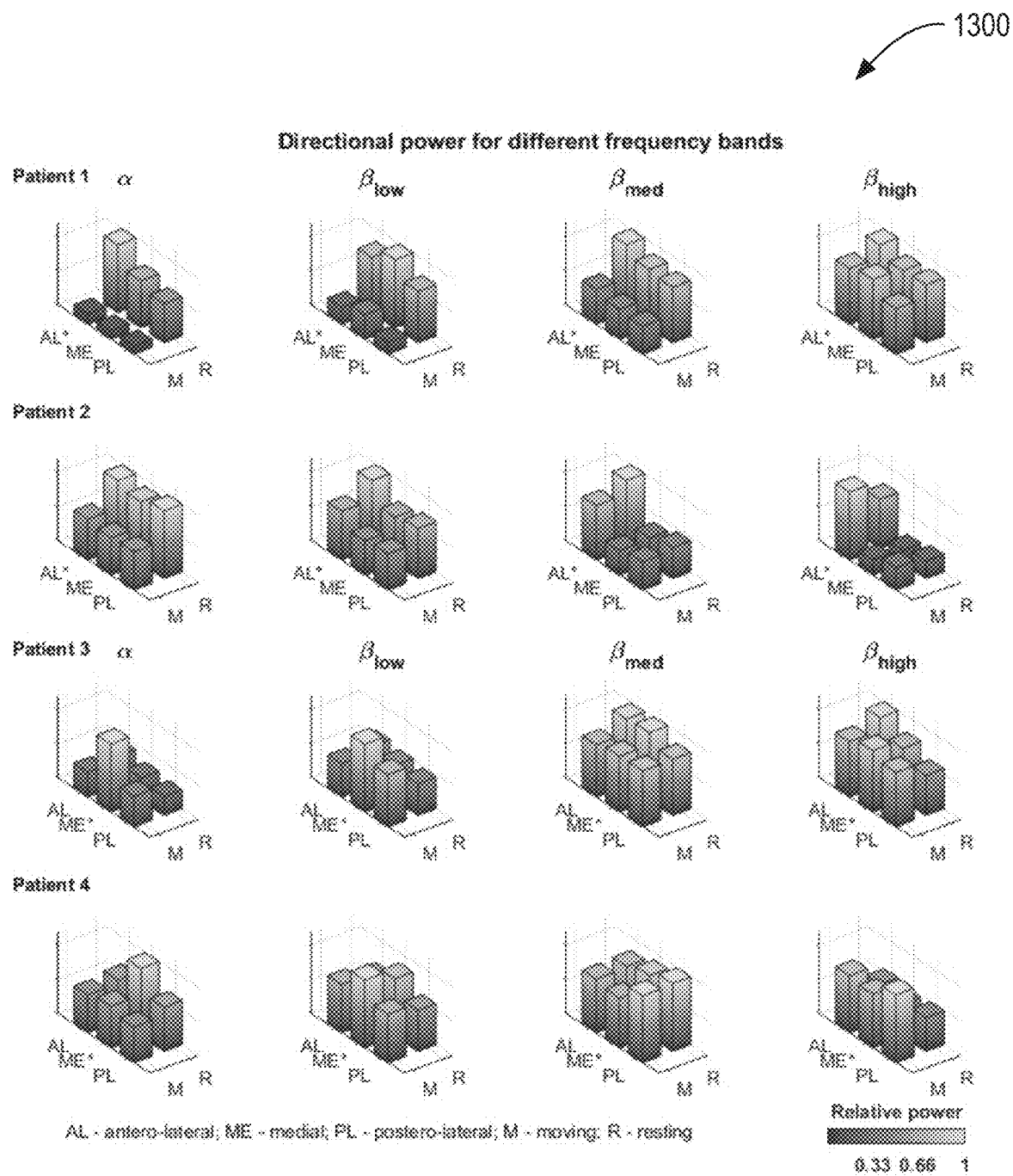

FIG. 13 illustrates a comparison 1300 of the spectral power for the two conditions in the different frequency bands. The first condition is moving and the second condition is resting. The comparison 1300 illustrates that subjects 1 and 2 had most power during resting across the four frequency bands, while subjects 3 and 4 had no preferable condition. For the medium beta frequency band, moving and resting had similar power in these two subjects.

The above plots in FIGS. 10-13 illustrate that the power spectral densities showed relevant activity between about 8 Hz and about 30 Hz. The beta band can be linked with motor functions and Parkinson's disease can be linked with an increase in beta oscillations in the subthalamic nucleus. On average the highest spectral power for medium and high beta bands was observed in the direction matching the 1st best stimulation direction, e.g., the direction with the largest therapeutic window.

Figure 14:
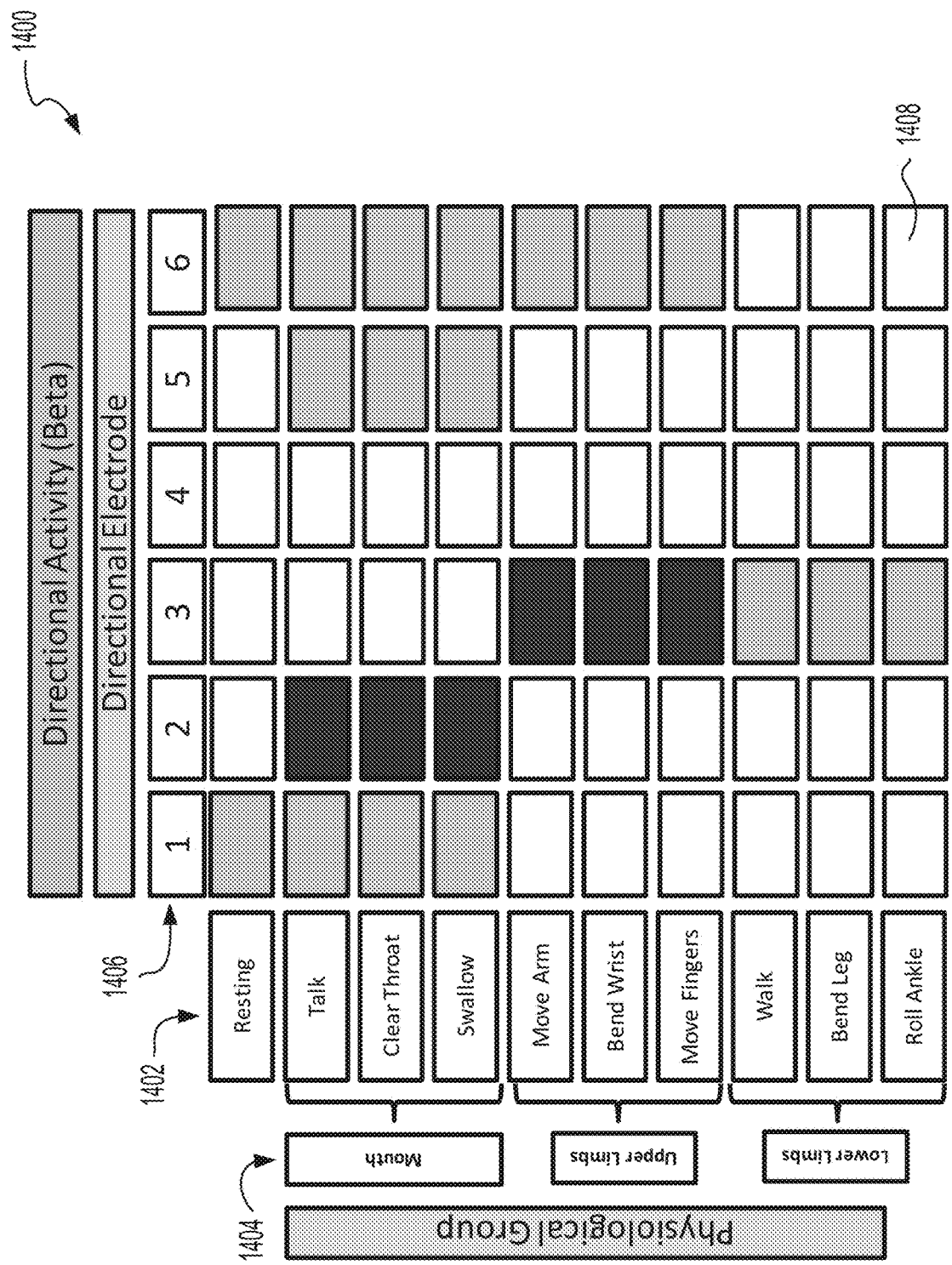
FIG. 14 illustrates an example heat map of the amount of beta activity recorded at each of the electrodes of the lead during a plurality of activities.

FIG. 14 illustrates an example heat map 1400 to illustrate the amount of beta activity recorded at each of the electrodes of the lead during a plurality of activities. The heat map 1400 can indicate the relative amount of beta activity recorded at each of the plurality of electrodes 1406. The amount of beta activity can be calculated or otherwise determined as described above in relation to FIGS. 9A-13, among others. For example, the recording patch can record neurological activity as the subject performs a plurality of activities as described in relation to FIG. 9B. As illustrated in FIG. 14, a test was performed where the amount of beta activity was identified at 6 different electrodes 1406. The electrodes 1406 can correspond to 6 electrodes of the lead 106. The controller can determine the beta activity as (or immediately after) the subject performs one of a plurality of activities 1402. The heat map 1400 can group the activities 1402 into groups 1404. The activities 1402 can be grouped based on the region of the body that is activated when performing the respective activity. For example, the movement of the arm, bending of the wrist, and movement of the fingers can be grouped into a group called "upper limbs." As illustrated in FIG. 14, the heat map 1400 illustrates the amount of beta activity as the subject: is at rest; talking, clearing the throat; and swallowing (the "mouth" group); moving the arm, bending the wrist, and moving the fingers (the "upper limb" group); and walking, bending the leg, and rolling the ankle (the "lower limb" group).

The heat map 1400 can be a matrix that visually illustrates, for each electrode 1406-activity 1402 combination, a value 1408 of beta activity detected by the recording patch. The value 1408 can be a color-coded indicator or a value-coded indicator. For example, as illustrated in FIG. 14, relatively low beta activity can be indicated by a lightly colored box and a relatively high beta activity can be indicated by a darkly colored box. The heat map 1400 can use any color mapping or other visual representation of values. For example, for a value-coded indicator, the value 1408 can be a scored value between 1 and 10 or a relative term such as "high," "medium," or "low." For each value 1408, the controller can normalize the value 1408 between 0 and 1 (or other value). For example, the controller can set the highest beta activity value 1408 of the electrode-activity combinations to 1 and the lowest beta activity value 1408 of the electrode-activity combinations to 0. The values between the highest and lowest electrode-activity combinations can be scaled between 0 and 1. The scaling can be linear, logarithmic, binary, normalized, or non-linear.

As illustrated in FIG. 14, directional electrodes 2 and 3 demonstrated a relatively high beta activity within the mouth and upper limb groups, respectively. Electrodes 1, 5, and 6 also demonstrated beta activity to a lesser extent. Electrode 4 did not demonstrate any beta activity. Based on the heat map 1400, the programmer could therefore conclude that directional electrode 2 may cause side effects linked to the mouth and throat region. However, the programmer could conclude that electrode 4 would be a good candidate for use in stimulation because of the low beta activity detected for each of electrode 4's electrode-activity combinations.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An implantable device, comprising:
    a housing to secure against a skull of a subject, the housing comprising:
        a first port configured to receive a connection from an implantable pulse stimulator outside the housing, the first port comprising a first plurality of connections;
        a second port configured to receive a connection from an implantable lead outside the housing, the second port comprising a second plurality of connections;
        a plurality of switches configured to:
            selectively interconnect, at a first time point, the first plurality of connections with the second plurality of connections to pass a stimulation signal from the implantable pulse stimulator to the implantable lead;
            selectively interconnect, at a second time point, the second plurality of connections with a recording module to pass a first biological signal; and
        the recording module configured to:
            generate a second biological signal based on the first biological signal received from the second plurality of connections; and
            transmit the second biological signal to a receiver outside the housing.

2. The device of claim 1, comprising the housing comprising:
    an antenna configured to wirelessly communicate with an antenna of the receiver; and
    the recording module configured to wirelessly transmit the amplified biological signal, via the antenna, to the antenna of the receiver.

3. The device of claim 1, wherein the recording module is configured to transmit the second biological signal to the receiver included in the implantable pulse stimulator.

4. The device of claim 1, comprising the housing comprising:
    an antenna configured to wirelessly receive electromagnetic power.

5. The device of claim 1, comprising:
the plurality of switches configured to selectively interconnect, at a third time point, a subset of the second plurality of connections with the recording module.

6. The device of claim 1, comprising:
the housing defining a pass-through port configured to receive a lead body of the implantable lead.

7. The device of claim 1, comprising:
the housing comprising a convex surface configured to conform to a surface of a subject's skull.

8. The device of claim 1, comprising the recording module is configured to transmit the second biological signal to the receiver, the receiver comprising a memory and one or more processors to:
determine a power level in a beta band of each of a plurality of amplified biological signals; and
select one of the second plurality of connections based on the power level in the beta band of each of the plurality of amplified biological signals.

9. The device of claim 1, the recording module to:
determine a power level in a beta band of each of a plurality of amplified biological signals; and
select one of the second plurality of connections based on the power level in the beta band of each of the plurality of amplified biological signals.

10. The device of claim 1, comprising a plurality of electrodes to receive a biological signal of a plurality of biological signals with a highest power level in a beta band.

11. A method, comprising:
implanting a recording patch against a skull of a subject, the recording patch comprising a housing, the housing comprising:
    a first port configured to receive a connection from an implantable pulse stimulator outside the housing, the first port comprising a first plurality of connections;
    a second port configured to receive a connection from an implantable lead comprising a plurality of electrodes outside the housing, the second port comprising a second plurality of connections;
    a plurality of switches in electrical communication with the first plurality of connections and the second plurality of connections; and
    a recording module;
coupling, with the plurality of switches, the second plurality of connections with the recording module;
receiving, at the second plurality of connections, a first biological signal from the implantable lead;
generating, by the recording module, a second biological signal based on the first biological signal;
determining at least one signal characteristic of the first biological signal; and
selecting an electrode of the plurality of electrodes based on the at least one signal characteristic of the first biological signal.

12. The method of claim 11, comprising:
coupling, with the plurality of switches, the first plurality of connections with the second plurality of connections; and
transmitting, from the implantable lead via the recording patch, a stimulation signal to the electrode of the plurality of electrodes.

13. The method of claim 12, comprising:
removing an external power supply from the recording patch prior to transmitting the stimulation signal to the electrodes of the plurality of electrodes.

14. The method of claim 11, comprising:
wirelessly powering the recording patch from a source external to the subject.

15. The method of claim 11, comprising:
transmitting the second biological signal to a receiver external to the subject; and
determining, by the receiver, the at least one signal characteristic of the second biological signal.

16. The method of claim 15, comprising:
wirelessly transmitting the second biological signal to the receiver external to the subject.

17. The method of claim 11, comprising:
connecting one of the second plurality of connections in electrical communication with the electrode of the plurality of electrodes to a connection of the plurality of connections receiving a stimulation signal.

18. The method of claim 11, wherein the at least one signal characteristic is a power level in a beta band of a plurality of amplified biological signals.

19. The method of claim 11, comprising:
determining a power level in a beta band of each of a plurality of amplified biological signals; and
selecting the electrode of the plurality of electrodes based on the power level in the beta band of each of the plurality of amplified biological signals.

20. The method of claim 11, wherein the electrode of the plurality of electrodes received a biological signal of a plurality of biological signals with a highest power level in a beta band.

* * * * *